(12) United States Patent
Porro et al.

(10) Patent No.: US 7,049,108 B2
(45) Date of Patent: May 23, 2006

(54) PROCESSES FOR PRODUCING LACTIC ACID USING YEAST TRANSFORMED WITH A GENE ENCODING LACTATE DEHYDROGENASE

(75) Inventors: Danilo Porro, Milan (IT); Michele Bianchi, Milan (IT); Bianca Maria Ranzi, Milan (IT); Laura Frontali, Milan (IT); Marina Vai, Milan (IT); Aaron Adrian Winkler, Milan (IT); Lilia Alberghina, Milan (IT)

(73) Assignee: Tate & Lyle Ingredients Americas, Inc., Decatur, IL (US)

( * ) Notice: Subject to any disclaimer, the term of this patent is extended or adjusted under 35 U.S.C. 154(b) by 241 days.

(21) Appl. No.: 10/068,137

(22) Filed: Feb. 6, 2002

(65) Prior Publication Data

US 2003/0032152 A1 Feb. 13, 2003

Related U.S. Application Data

(62) Division of application No. 09/508,277, filed as application No. PCT/EP98/05758 on Sep. 11, 1998, now Pat. No. 6,429,006.

(30) Foreign Application Priority Data

Sep. 12, 1997 (IT) ............................. MI97A2080

(51) Int. Cl.
*C12P 7/56* (2006.01)
(52) U.S. Cl. ..................... 435/139; 435/135; 435/254.2
(58) Field of Classification Search ............... 435/135, 435/254.2
See application file for complete search history.

(56) References Cited

U.S. PATENT DOCUMENTS

| | | | |
|---|---|---|---|
| 2,024,565 A | 12/1935 | Braun | 260/119 |
| 4,885,247 A | 12/1989 | Datta | 435/139 |
| 5,068,418 A | 11/1991 | Kulprathipanja et al. | 562/580 |
| 5,464,760 A | 11/1995 | Tsai et al. | 435/139 |
| 5,503,750 A | 4/1996 | Russo, Jr. et al. | 210/641 |
| 5,510,526 A | 4/1996 | Baniel et al. | 562/580 |
| 5,574,180 A | 11/1996 | McQuigg et al. | 558/147 |
| 5,641,406 A | 6/1997 | Sarhaddar et al. | 210/656 |
| 5,780,678 A | 7/1998 | Baniel et al. | 562/580 |
| 5,892,109 A | 4/1999 | Baniel et al. | 562/580 |
| 5,959,144 A | 9/1999 | Baniel | 562/580 |
| 6,001,255 A | 12/1999 | Eyal et al. | 210/638 |
| 6,087,532 A | 7/2000 | Baniel et al. | 562/580 |
| 6,160,173 A | 12/2000 | Eyal et al. | 562/589 |
| 6,187,951 B1 | 2/2001 | Baniel et al. | 562/580 |
| 6,229,046 B1 | 5/2001 | Eyal et al. | 562/589 |
| 6,268,189 B1 | 7/2001 | Skory | 435/139 |
| 6,280,985 B1 | 8/2001 | Caboche et al. | 435/139 |
| 6,319,382 B1 | 11/2001 | Norddahl | 204/530 |
| 6,320,077 B1 | 11/2001 | Eyal et al. | 562/589 |
| 6,429,006 B1 | 8/2002 | Porro et al. | 435/254 |
| 6,475,759 B1 | 11/2002 | Carlson et al. | 435/139 |
| 6,485,947 B1 | 11/2002 | Rajgarhia et al. | 435/139 |
| 6,489,508 B1 | 12/2002 | Van Gansbeghe et al. | 562/589 |
| 2003/0228671 A1 | 12/2003 | Hause et al. | 435/161 |
| 2004/0029238 A1 | 2/2004 | Rajgarhia et al. | 435/139 |
| 2004/0029256 A1 | 2/2004 | Rajgarhia et al. | 435/254.2 |

FOREIGN PATENT DOCUMENTS

| | | |
|---|---|---|
| EP | 0 932 593 B1 | 4/2002 |
| WO | WO94/00554 | 1/1994 |
| WO | WO94/01569 | 1/1994 |
| WO | WO 99/14335 | 3/1999 |
| WO | WO 99/19503 | 4/1999 |
| WO | WO 00/71738 A1 | 11/2000 |
| WO | WO 01/25180 | 4/2001 |
| WO | WO 02/42471 | 5/2002 |
| WO | WO 03/102152 A2 | 12/2003 |
| WO | WO 03/102200 A2 | 12/2003 |
| WO | WO 03/102201 A2 | 12/2003 |

OTHER PUBLICATIONS

Adachi et al. Modification of metabolic pathways of *Saccharomyces cerevisiae* by the expression of lactate dehydrogenase and deletion of pyruvate decarboxylase genes for the lactic acid fermentation at low pH value. J. of Fermentation and Bioengineering (1998) 86(3): 284-289.*
Porro et al., "Development of Metabolically Engineered *Saccharomyces cerevisiae* Cells for the Production of Lactic Acid," *Biotechnology Progress* 11:294-298 (1995).
"Production of Pyruvic Acid by Fermentation—Comprises Culturing Mutant of Torulopsis with Reduced Pyruvate Decarboxylase Activity," Derwent Publications Ltd., Abstract No. J63258586.

(Continued)

*Primary Examiner*—Kathleen M. Kerr
*Assistant Examiner*—Hope Robinson
(74) *Attorney, Agent, or Firm*—Williams, Morgan & Amerson, P.C.

(57) ABSTRACT

Yeast strains transformed with at least one copy of a gene coding for lactic dehydrogenase (LDH) and further modified for the production of lactic acid with high yield and productivities, are described.

9 Claims, 12 Drawing Sheets

OTHER PUBLICATIONS

Davis et al., "A Yeast Cyclophilin Gene Essential for Lactate Metabolism at High Temperature," *Proceedings of the National Academy of Sciences of USA* 89:11169-11173 (1992).

Stewart, "A Chemist's Perspective on the Use of Genetically Engineered Microbes as Reagents for Organic Synthesis," *Biotechnology and Genetic Engineering Reviews* 14:67-143 (1997).

GenBank Accession No. M76708. *L. casei* lactate dehydrogenase (ldg) gene, complete cds. Created Oct. 23, 1991.

GenBank Accession No. M22305. *B. megaterium* L-lactate dehydrogenase gene. Created Sep. 15, 1990.

GenBank Accession No. M19396. *B.stearothermophilus* lactate dehydrogenase (LDH) gene, complete cds. Created Sep. 15, 1990.

GenBank Accession No. AF023920. Kluyveromyces lactis pyruvate dehydrogenase complex E1-alpha subunit (PDA1) gene, complete cds. Created Oct. 24, 1997.

GenBank Accession No. U24155. *Saccharomyces cerevisiae* carboxylic acid transporter protein homolog (JEN1) gene, complete cds. Created Apr. 26, 1995.

Zeeman, A. M. et al., "Inactivation of the Kluyveromyces lactis KlPDA1 gene leads to loss of pyruvate dehydrogenase activity, impairs growth on glucose and triggers aerobic alcoholic fermentation," In: *Microbiology* 144, (Pt 12), pp. 3437-3446, 1998.

Zülli, F. et al., "Nucleotide sequences of lactate dehydrogenase genes from the thermophilic bacteria *Bacillus stearothermophilus, B. caldolyticus* and *B.caldotenax*," In: *Biol. Chem.*, Hoppe-Seyler, 368, pp. 1167-1177, 1987.

Waldvogel, S. et al., "Nucleotide sequence of the L-lactate dehydrogenase gene from the mesophilic bacterium *B.megaterium*. Preparation and properties of a hybrid lactate dehydrogenase comprising moieties of the *B. megaterium* and *B.stearothermophilus* enzymes," In: *Biol. Chem.*, Hoppe-Seyler, 368, pp. 1391-1399,1987.

Kim, S.F., et al., "Cloning and nucleotide sequence of the *Lactobacillus casei* lactate dehydrogenase gene," In: *Appl. Environ. Microbiol.*, 57, pp. 2413-2417, 1991.

Chang et al., "Homofermentative Production of D- or L-Lactate in Metabolically Engineered *Escherichia coli* RR1," *Applied Environ. Microbiol.*, 65(4):1384-1389, 1999.

Hohmann, "Pyruvate Decarboxylases," In *"Yeast Sugar Metabolism"*, 11:187-211, 1997.

Skory, Isolation and Expression of Lactate Dehydrogenase Genes from *Rhizopus Oryzae*, *Applied Inviron. Microbiol.*, 66(6):2343-2348, 2000.

Zhou et al., Production of Optically Pure D-Lactic Acid in Mineral Salts Medium by Metabolically Engineered *Escherichia coli* W3110, *Applied Environ. Microbiol.* 69(1):399-407, 2003.

Genga et al., "Mitochondrial NAD, L-Lactate Dehydrogenase and NAD, D-Lactate Dehydrogenase in the Yeast *Saccharomyces cerevisiae*," *Microbiologica* 6(1):1-8 (1983) (Abstract).

Goffin et al., "Lactate Dehydrogenase-Independent Lactic Acid Racemization in *Lactobacillus* Plantarum" (2003) (Abstract, Mtg., *Belgian Soc. of Biochem. and Molec. Biol.*, Feb. 14, 2003).

Skory, "Lactic Acid Production by *Saccharomyces cerevisiae* Expressing a *Rhizopus oryzae* Lactate Dehydrogenase Gene," *J. Ind. Microbiol. Biotechnol.*, 30:22-27 (2003).

Chelstowska et al., *Yeast* 15(13):1377-1391 (1999).

Garvie, *Microbiological Reviews* 44(1):106-139 (Mar. 1980).

Lodi et al., *Mol. Gen. Genet.* 238:315-324 (1993).

Pallotta et al., *Biochimica et Biophysica Acta* 1608:104-113 (2004).

\* cited by examiner

Figure 7A,B
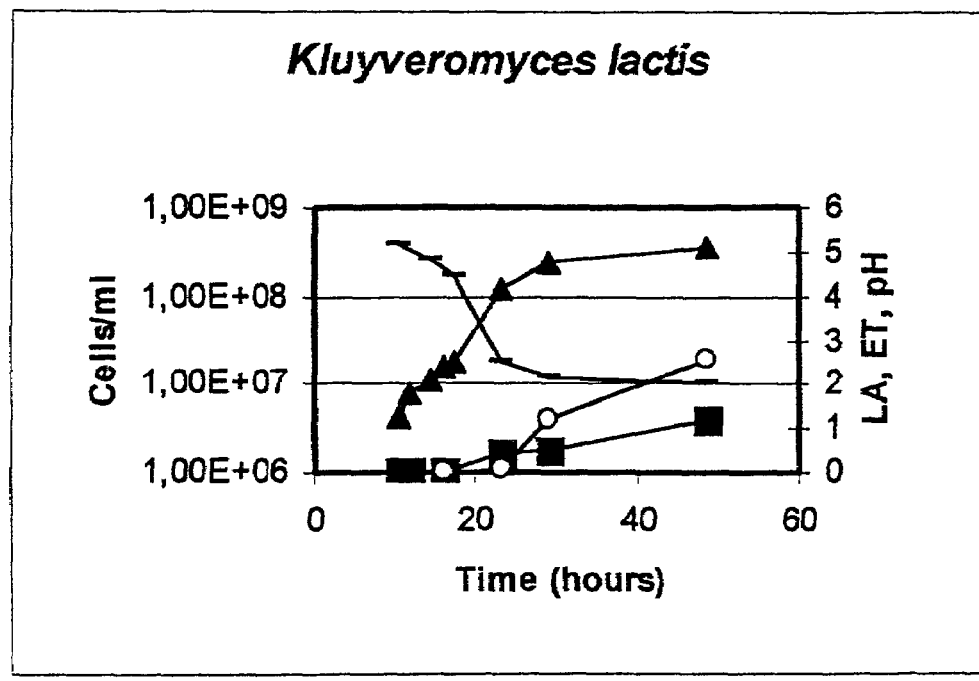
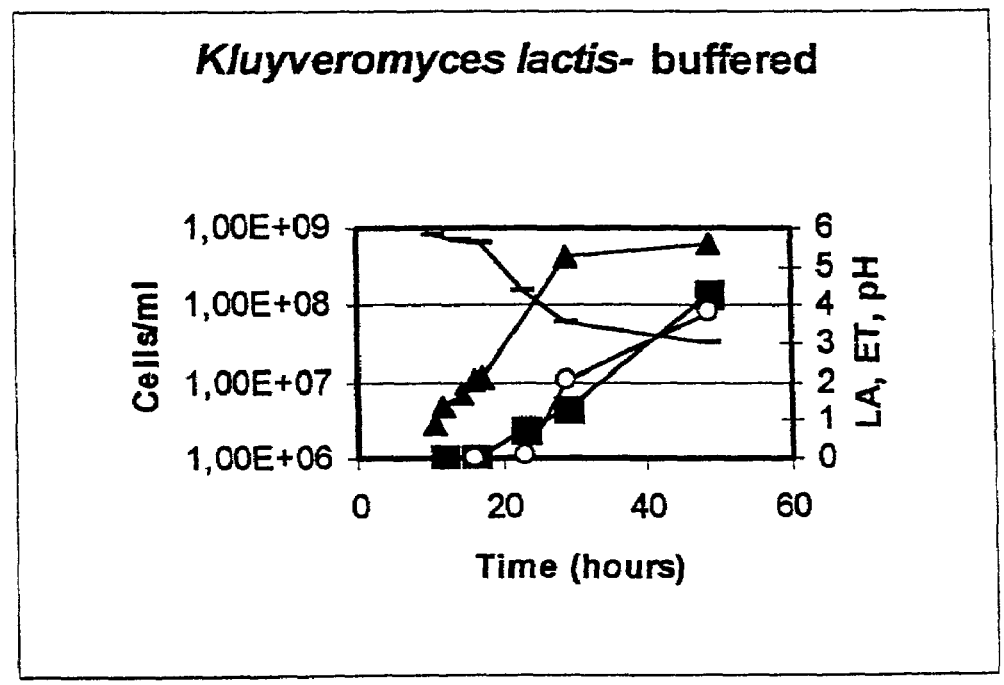

Figure 8A, B
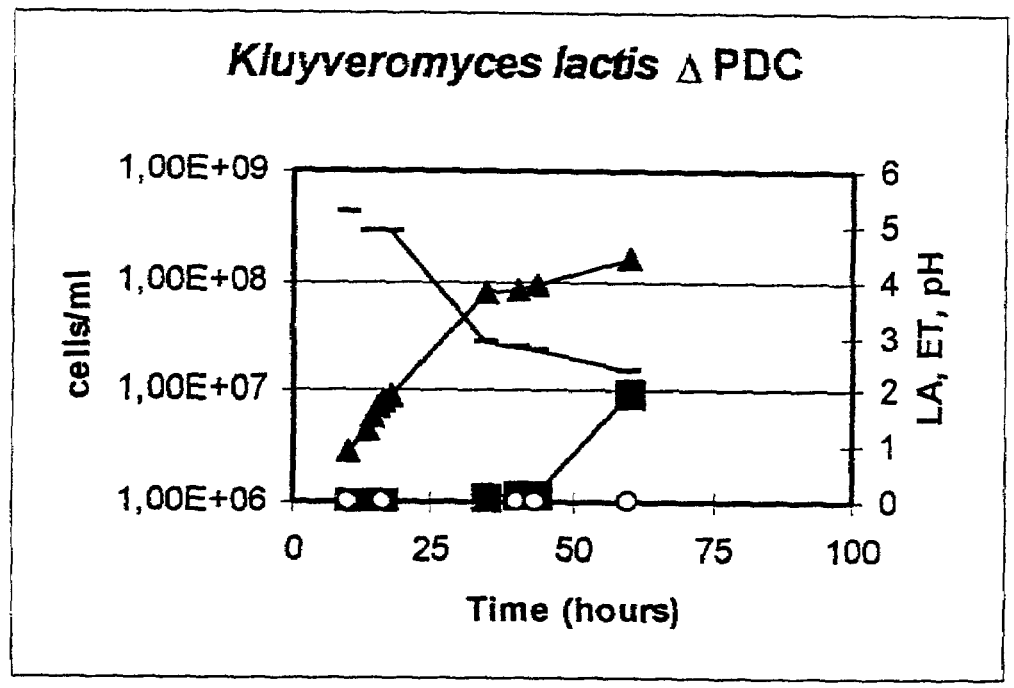
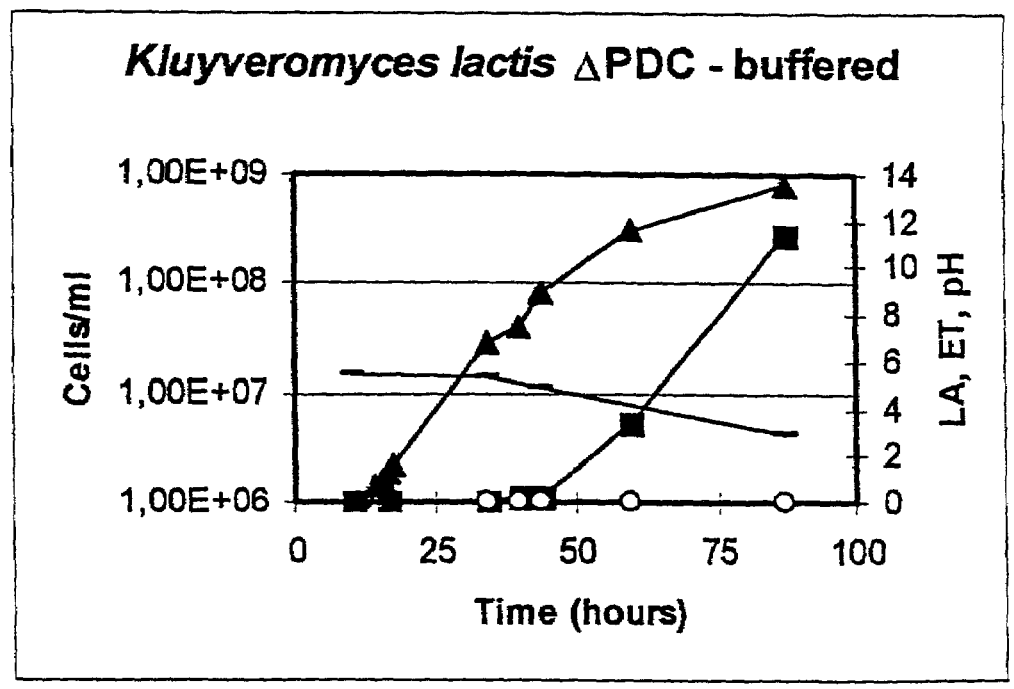

Figure 9A, B
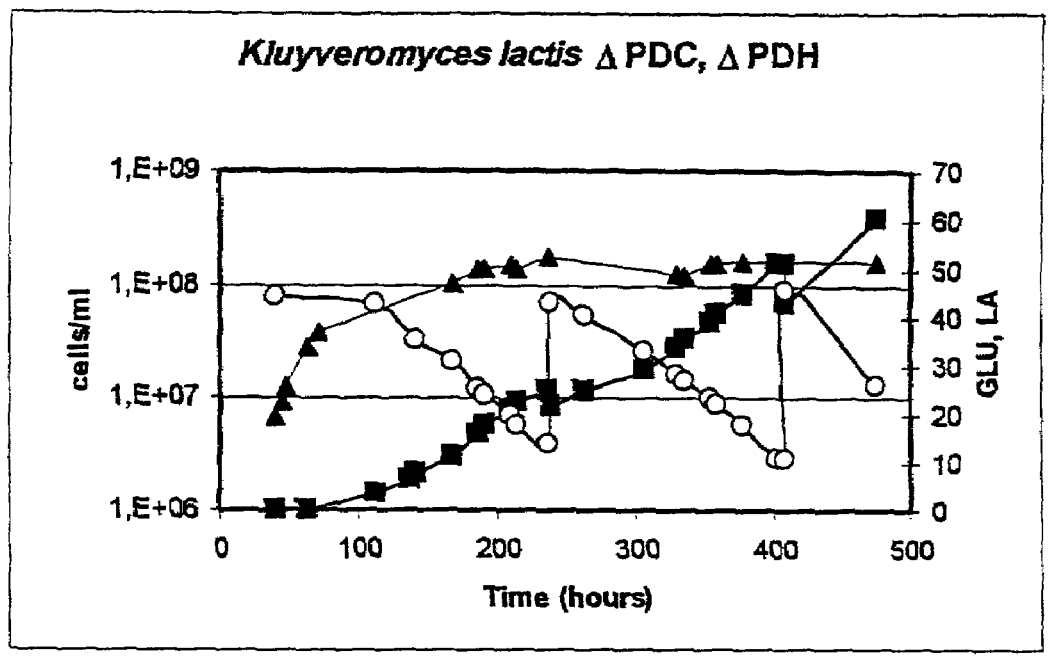
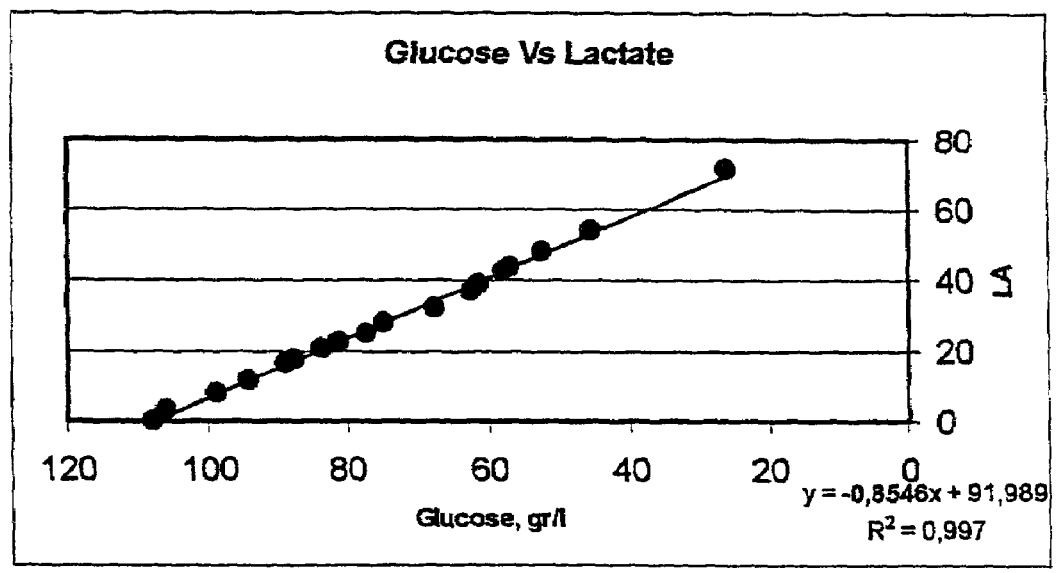

PROCESSES FOR PRODUCING LACTIC ACID USING YEAST TRANSFORMED WITH A GENE ENCODING LACTATE DEHYDROGENASE

This application is a divisional of application Ser. No. 09/508,277, having a 35 U.S.C. §102(e) date of Jun. 29, 2000, issued as U.S. Pat. No. 6,429,006 on Aug. 6, 2002, which is a 35 U.S.C. §371 national phase entry of PCT/EP98/05758, filed Sep. 11, 1998.

The invention refers to yeast strains transformed with at least one copy of a gene coding for lactic dehydrogenase (LDH) and further modified for the production of lactic acid with high yield and productivity.

BACKGROUND OF THE INVENTION

The applications of lactic acid and its derivatives encompass many fields of industrial activities (i.e., chemistry, cosmetic, and pharmacy), as well as important aspects of food manufacture and use. Furthermore, today there is growing interest in the production of such an organic acid to be used directly for the synthesis of biodegradable polymer materials.

Lactic acid may be produced by chemical synthesis or by fermentation of carbohydrates using microorganisms. The latter method is now commercially preferred because microorganisms have been developed that produce exclusively one isomer, as opposed to the racemic mixture generated by chemical synthesis. The most important industrial microorganisms, such as species of the genera *Lactobacillus, Bacillus*, and *Rhizopus*, produce L(+)-lactic acid. Production by fermentation of D(−)-lactic acid or mixtures of L(+)- and D(−)-lactic acid are also known.

During a typical lactic acid fermentation, there is an inhibitory effect caused by lactic acid produced on the metabolic activities of the producing microorganism. Besides the presence of lactic acid, lowering the pH value also inhibits cell growth and metabolic activity. As a result, the extent of lactic acid production is greatly reduced.

Therefore, the addition of $Ca(OH)_2$, $CaCO_3$, NaOH, or $NH_4OH$ to neutralise the lactic acid and to thereby prevent the pH decrease is a conventional operation in industrial processes to counteract the negative effects of free lactic acid accumulation.

These processes allow the production of lactate(s) by maintaining the pH at a constant value in the range of about 5 to 7; this is well above the $pK_a$ of lactic acid, 3.86.

Major disadvantages are connected to the neutralisation of lactic acid during the fermentation. Mainly, additional operations are required to regenerate free lactic acid from its salt and to dispose of or recycle the neutralising cation; this is an expensive process. All the extra operations and expense could be eliminated if free lactic acid could be accumulated by microorganisms growing at low pH values, thus minimising the production of lactate(s).

It has been proposed the use of recombinant yeasts expressing the lactate dehydrogenase gene so as to shift the glycolytic flux towards the production of lactic acid.

FR-A-2 692 591 (Institut Nationale la Recherche Agronomique) discloses yeast strains, particularly *Saccharomyces* strains, containing at least one copy of a gene coding for a lactate dehydrogenase from a lactic bacterium, said gene being under the control of sequences regulating its expression in yeasts.

Said strains may give both the alcoholic and the lactic fermentation and this so called "intermediate" or "balanced" fermentation could be exploited in areas such as brewing, enology, and baking.

Porro et al., (Biotechnol. Prog. 11, 294–298, 1995) have also reported the transformation of *S. cerevisiae* with a gene coding for bovine lactate dehydrogenase.

However, because of the high production of ethanol, the yield in the production of lactic acid for both the processes described was not considered to be competitive with that obtainable by the use of lactic bacteria.

In the past decade, "non conventional yeasts" other than *S. cerevisiae* have gained considerable industrial interest as host for the expression of heterologous proteins. Examples are the methanol-utilising yeasts such as *Hansenula polimorpha* and *Pichia pastoris*, the lactose-utilizing yeasts such as *Kluyveromyces lactis*. In addition to enabling the use of a wider range of substrates as carbon and energy sources, other arguments have been put forward to the industrial use of "non conventional yeasts". Generally speaking, biomass and product-yield are less affected, in some of these yeasts, by extreme conditions of the cellular environment. High-sugar-tolerant (i.e., 50–80% w/v glucose medium; *Torulaspora*-syn. *Zygosaccharomyces-delbrueckii, Zygosaccharomyces rouxii* and *Zygosaccharomyces bailii*; Ok T and Hashinaga F., Journal of General & Applied Microbiology 43(1): 39–47, 1997) and acid- and lactic-tolerant (*Zygosaccharomyces rouxii* and *Zygosaccharomyces bailii*; Houtsma PC, et al., Journal of Food Protection 59(12), 1300–1304, 1996.) "non conventional yeasts" are available. As already underlined the cost of down stream processing could be strongly reduced if the fermentation process is carried out under one or more of the above mentioned "extreme conditions".

SUMMARY OF THE INVENTION

According to a first embodiment, this invention provides yeast strains lacking ethanol production ability or having a reduced ethanol production ability and transformed with at least one copy of a gene coding for lactic dehydrogenase (LDH) functionally linked to promoter sequences allowing the expression of said gene in yeasts.

More particularly, this invention provides yeast strains having a reduced pyruvate dehydrogenase activity and a reduced pyruvate decarboxylase activity and transformed with at least one copy of a gene coding for lactic dehydrogenase (LDH) functionally linked to promoter sequences allowing the expression of said gene in yeasts.

According to another embodiment, this invention provides yeast strains of *Kluyveromyces, Torulaspora* and *Zygosaccharomyces* species, transformed with at least one copy of a gene coding for lactic dehydrogenase (LDH) functionally linked to promoter sequences allowing the expression of the gene in said yeasts.

According to a further embodiment, the invention also provides yeast cells transformed with a heterologous LDH gene and overexpressing a lactate transporter.

Other embodiments are the expression vectors comprising a DNA sequence coding for a lactic dehydrogenase functionally linked to a yeast promoter sequence and a process for the preparation of DL-, D- or L-lactic acid by culturing the above described metabolically engineered yeast strains in a fermentation medium containing a carbon source and recovering lactic acid from the fermentation medium.

Furthermore, the invention provides processes for improving the productivity (g/l/hr), production (g/l) and yield (g/g) on the carbon source of lactic acid by culturing said yeast strains in a manipulated fermentation medium and recovering lactic acid from the fermentation medium.

DESCRIPTION OF THE INVENTION

It has been found that production of lactic acid can be obtained by metabolically modified yeasts belonging to the genera *Kluyveromyces, Saccharomyces, Torulaspora* and *Zygosaccharomyces*.

More particularly, it has been found that very high yields in the production of lactic acid are obtained by engineered yeast strains so as to replace at least the ethanolic fermentation by lactic fermentation.

Even higher yields (>80% g/g) in the production of lactic acid may be obtained by engineered yeast strains so as to replace both the ethanolic fermentation and the use of pyruvate by the mitochondria by lactic fermentation.

To this purpose, the invention also provides transformed yeast cells having an increased LDH activity, for instance as a consequence of an increased LDH copy number per cell or of the use of stronger promoters controlling LDH expression.

An increased LDH copy number per cell means at least one copy of a nucleic acid sequence encoding for lactic dehydrogenase protein, preferably at least two copies, more preferably four copies or, even more preferably, at least 10–50 copies of said nucleic acid sequence.

In order to have the highest production of lactic acid, yeast cells transformed according to the invention preferably overexpress a lactate transporter. This can be obtained by transforming yeast cells with one or more copies of a gene required for lactate transport.

The strains according to the invention can be obtained by several methods, for instance by genetic engineering techniques aiming at the expression of a lactate dehydrogenase activity, and by inactivating or suppressing enzymatic activities involved in the production of ethanol, e.g. pyruvate decarboxylase and alcohol dehydrogenase activities, and by inactivating or suppressing enzymatic activities involved in the utilisation of pyruvate by the mitochondria.

Since pyruvate decarboxylase catalyses the first step in the alcohol pathway, yeast strains without or having a substantially reduced pyruvate decarboxylase (PDC) activity and expressing a heterologous lactate dehydrogenase gene are preferred.

Further, since pyruvate dehydrogenase catalyzes the first step in the utilization of pyruvate by the mitochondria, yeast strains having no or a substantially reduced pyruvate dehydrogenase (PDH) activity and expressing a heterologous lactate dehydrogenase gene are also preferred.

Since lactate is excreted in the medium via a lactate transporter, cells producing lactic acid and overexpressing the lactate transporter are also preferred.

The expression of a LDH gene in yeast strains allows the production of lactic acid at acid pH values so that the free acid is directly obtained and the cumbersome conversion and recovery of lactate salts are minimized. In this invention, the pH of the fermentation medium may initially be higher than 4.5, but will decrease to a pH of 4.5 or less, preferably to a pH of 3 or less at the termination of the fermentation.

Any kind of yeast strain may be used according to the invention, but *Kluyveromyces, Saccharomyces Torulaspora* and *Zygosaccharomyces* species are preferred because these strains can grow and/or metabolize at very low pH, especially in the range of pH 4.5 or less; genetic engineering methods for these strains are well-developed; and these strains are widely accepted for use in food-related applications.

Good yields of lactic acid can moreover be obtained by *Kluyveromyces, Torulaspora* and *Zygosaccharomyces* strains transformed with a gene coding for lactic dehydrogenase having a "wild-type" pyruvate decarboxylase and/or a pyruvate dehydrogenase activity.

The term "reduced pyruvate decarboxylase activity" means either a decreased concentration of enzyme in the cell or reduced or no specific catalytic activity of the enzyme.

The term "reduced pyruvate dehydrogenase activity" means either a decreased concentration of enzyme in the cell or reduced or no specific catalytic activity of the enzyme.

According to the invention, it is preferred the use of strains wherein the ethanol production is or approaches zero but a reduced production for instance at least 60% lower, preferably at least 80% lower and even more preferably at least 90% lower than the normal of wild-type strains is acceptable.

According to the invention, it is preferred the use of strains wherein the pyruvate decarboxylase and/or pyruvate dehydrogenase activities are or approach zero but a reduced activity for instance at least 60% lower, preferably at least 80% lower and even more preferably at least 90% lower than the normal of wild-type strains is acceptable.

An example of *K. lactis* having no PDC activity has been disclosed in Mol. Microbiol. 19 (1), 27–36, 1996.

Examples of *Saccharomyces* strains having a reduced PDC activity are available from ATCC under Acc.No. 200027 and 200028. A further example of a *Saccharomyces* strain having a reduced PDC activity as a consequence of the deletion of the regulatory PDC2 gene has been described in Hohmann S (1993)(*Mol Gen Genet* 241:657–666).

An example of a *Saccharomyces* strain having no PDC activity has been described in Flikweert M. T. et al. (Yeast, 12:247–257, 1996). In *S. cerevisiae* reduction of the PDC activity can be obtained either by deletion of the structural genes (PDC1, PDC5, PDC6) or deletion of the regulatory gene (PDC2).

An example of *Kluyveromyces* strain having no PDH activity has been described in Zeeman et al. (Genes involved in pyruvate metabolism in *K. lactis*; Yeast, vol 13 Special Issue April 1997, Eighteenth International Conference on Yeast Genetics and Molecular Biology, p143).

An example of *Saccharomyces* strain having no PDH activity has been described in Pronk J T. et al. (Microbiology. 140 (Pt 3):601–10, 1994).

PDC genes are highly conserved among the different yeast genera (Bianchi et al., Molecular Microbiology, 19(1): 27–36, 1996; Lu P. et al., Applied & Environmental Microbiology, 64(1):94–7, 1998). Therefore it can be easily anticipated that following classical molecular approaches, as reported by Lu P. et al. (supra), it is possible to identify, to clone and to disrupt the gene(s) required for a pyruvate decarboxylase activity from both *Torulaspora* and *Zygosaccharomyces* yeast species. Further, it can be also anticipated that following the same classical approaches, as reported by Neveling U. et al. (1998, Journal of Bacteriology, 180(6): 1540–8, 1998), it is possible to isolate, to clone and to disrupt the gene(s) required for the PDH activity in both *Torulaspora* and *Zygosaccharomyces* yeast species.

The pyruvate decarboxylase activity can be measured by known methods, e.g. Ulbrich J., Methods in Enzymology, Vol. 18, p. 109–115, 1970, Academic Press, New York.

The pyruvate dehydrogenase activity can be measured by known methods, e.g. according to Neveling U. et al. (supra).

Suitable strains can be obtained by selecting mutations and/or engineering of wild-type or collection strains. Hundreds of mutants could be selected by "high throughput screen" approaches. The modulation of pyruvate decarboxylase activity by using nutrients supporting different glycolytic flow rates (Biotechnol. Prog. 11, 294–298, 1995) did not prove to be satisfactory.

A preferred method for decreasing or destroying the pyruvate decarboxylase activity and/or pyruvate dehydrogenase activity in a yeast strain according to the invention consists in the deletion of the corresponding gene or genes.

These deletions can be carried out by known methods, such as that disclosed in Bianchi et al., (Molecular Microbiol. 19 (1),27–36, 1996; Flikweert M. T. et al., Yeast, 12:247–257, 1996 and Pronk J T. et al., Microbiology. 140 (Pt 3):601–10, 1994), by deletion or insertion by means of selectable markers, for instance the URA3 marker, preferably the URA3 marker from *Saccharomyces cerevisiae*. Alternatively, deletions, point-mutations and/or frame-shift mutations can be introduced into the functional promoters and genes required for the PDC and/or PDH activities. These techniques are disclosed, for instance, in Nature, 305, 391–397, 1983. An addition method to reduce these activities could be the introduction of STOP codons in the genes sequences or expression of antisense mRNAs to inhibit translation of PDC and PDH mRNAs.

A *Kluyveromyces lactis* strain wherein the PDC gene has been replaced by the URA3 gene of *S. cerevisiae* has already been described in Molecular Microbiology 19(1), 27–36, 1996.

The gene coding for lactate dehydrogenase may be of any species (e.g. mammalian, such as bovine, or bacterial), and it may code for the L(+)-LDH or the D(-)-LDH. Alternatively, both types of LDH genes may be expressed simultaneously. Further, any natural or synthetic variants of LDH DNA sequences, any DNA sequence with high identity to a wild-type LDH gene, any DNA sequence complementing the normal LDH activity may be used.

As transporter gene, for example the JEN1 gene, encoding for the lactate transporter of *S. cerevisiae*, can be used.

The transformation of the yeast strains can be carried out by means of either integrative or replicative vectors, linear or plasmidial.

The recombinant cells of the invention can be obtained by any method allowing a foreign DNA to be introduced into a cell (Spencer J f, et al., Journal of Basic Microbiology 28(5): 321–333, 1988), for instance transformation, electroporation, conjugation, fusion of protoplasts or any other known technique. Concerning transformation, various protocols have been described: in particular, it can be carried out by treating the whole cells in the presence of lithium acetate and of polyethylene glycol according to Ito H. et al. (J. Bacteriol., 153:163, 1983), or in the presence of ethylene glycol and dimethyl sulphoxyde according to Durrens P. et al. (Curr. Genet., 18:7, 1990). An alternative protocol has also been described in EP 361991. Electroporation can be carried out according to Becker D. M. and Guarente L. (Methods in Enzymology, 194:18, 1991).

The use of non-bacterial integrative vectors may be preferred when the yeast biomass is used, at the end of the fermentation process, as stock fodder or for other breeding, agricultural or alimentary purposes.

In a particular embodiment of the invention, the recombinant DNA is part of an expression plasmid which can be of autonomous or integrative replication.

In particular, for both *S. cerevisiae* and *K. lactis*, autonomous replication vectors can be obtained by using autonomous replication sequences in the chosen host. Especially, in yeasts, they can be replication origins derived from plasmids (2μ, pKD1, etc.) or even chromosomal sequence (ARS).

The integrative vectors can be obtained by using homologous DNA sequences in certain regions of the host genome, allowing, by homologous recombination, integration of the vector.

Genetic tools for gene expression are very well developed for *S. cerevisiae* and described in Romanos, M. A. et al. Yeast, 8:423, 1992. Genetic tools have been also developed to allow the use of the yeasts *Kluyveromyces* and *Torulaspora* species as host cells for production of recombinant proteins (Spencer J f, et al., supra: Reiser J. et al., Advances in Biochemical Engineering-Biotechnology. 43, 75–102, 1990). Some examples of vectors autonomously replicating in *K. lactis* are reported, either based on the linear plasmid pKG1 of *K. lactis* (de Lovencourt L. et al. J. Bacteriol., 154:737, 1982), or containing a chromosomal sequence of *K. lactis* itself (KARS), conferring to the vector the ability of self replication and correct segregation (Das S., Hollenberg C. P., Curr. Genet., 6:123, 1982). Moreover, the recognition of a 2μ-like plasmid native to *K. drosophilarum* (plasmid pKD1—U.S. Pat. No. 5,166,070) has allowed a very efficient host/vector system for the production of recombinant proteins to be established (EP-A-361 991). Recombinant pKD1-based vectors contain the entire original sequence, fused to appropriate yeast and bacterial markers. Alternatively, it is possible to combine part of pKD1, with common *S. cerevisiae* expression vectors (Romanos M. A. et al. Yeast, 8:423, 1992)(Chen et al., Curr. Genet. 16: 95, 1989).

It is known that the 2μ plasmid from *S. cerevisiae* replicates and is stably maintained in *Torulaspora*. In this yeast the expression of heterologous protein(s) has been obtained by a co-transformation procedure, i.e. the simultaneous presence of an expression vector for *S. cerevisiae* and of the whole 2μ plasmid. (Compagno C. et al., Mol. Microb., 3:1003–1010, 1989). As a result of inter and intra molecular recombinations, it is possible to isolate a hybrid plasmid, bearing the complete 2μ sequence and the heterologous gene; such a plasmid is in principle able to directly transform *Torulospora*.

Moreover, an episomal plasmid based on *S. cerevisiae* ARS1 sequence has also been described, but the stability of this plasmid is very low, Compagno et al. (supra).

Recently, an endogenous, 2μ-like plasmid named pTD1 has been isolated in *Torulaspora* (Blaisonneau J. et al., Plasmid, 38:202–209, 1997); the genetic tools currently available for *S. cerevisiae* can be transferred to the new plasmid, thus obtaining expression vectors dedicated to *Torulaspora* yeast species.

Genetic markers for *Torulaspora* yeast comprise, for instance, URA3 (Watanabe Y. et al., FEMS Microb. Letters, 145:415–420, 1996), G418 resistence (Compagno C. et al., Mol. Microb., 3:1003–1010, 1989), and cicloheximide resistance (Nakata K. et Okamura K., Biosc.Biotechnol.Biochem., 60:1686–1689, 1996).

2μ-like plasmids from *Zygosaccharomyces* species are known and have been isolated in *Z. rouxii* (pSR1), in *Z. bisporus* (pSB3), in *Z. fermentati* (pSM1) and in *Z. bailii* (pSB2) (Spencer J F. et al., supra).

Plasmid pSR1 is the best known: it is replicated in *S. cerevisiae*, but 2μ ARS are not recognized in *Z. rouxii* (Araki H. and Hoshima Y., J.Mol. Biol., 207:757–769, 1989).

Episomal vectors based on *S. cerevisiae* ARS1 are described for *Z. rouxii* (Araki et al., Mol Gen.Genet., 238: 120–128, 1993).

A selective marker for *Zygosaccharomyces* is the gene APT1 allowing growth in media containing G418 (Ogawa et al., Agric.Biol.Chem., 54:2521–2529, 1990).

Any yeast promoter, either inducible or constitutive, may be used according to the invention. To date, promoters used for the expression of proteins in *S. cerevisiae* are well described by Romanos et al. (supra). Promoters commonly used in foreign protein expression in *K. lactis* are *S. cerevisiae* PGK and PHO5 (Romanos et al., supra), or homologous promoters, such as LAC4 (van den Berg J. A. et al., BioTechnology, 8:135, 1990) and KlPDC (U.S. 5,631,143). The promoter of pyruvate decarboxylase gene of *K. lactis* (KlPDC) is particularly preferred.

Vectors for the expression of heterologous genes which are particularly efficient for the transformation of *Kluyveromyces lactis* strains are disclosed in U.S. Pat. No. 5,166,070, which is herein incorporated by reference.

Pyruvate decarboxylase gene promoters, preferably from *Kluyveromyces* species and even more preferably from *Kluyveromyces lactis*, disclosed in Molecular Microbiol. 19(1), 27–36, 1996, are particularly preferred. Triose phosphate isomerase and alcohol dehydrogenase promoters, preferably from *Saccharomyces* species and even more preferably from *Saccharomyces cerevisiae*, are also preferred (Romanos et al, supra).

For the production of lactic acid, the yeast strains of the invention are cultured in a medium containing a carbon source and other essential nutrients, and the lactic acid is recovered at a pH of 7 or less, preferably at a pH of 4.5 or less, and even more preferably at a pH of 3 or less. Since the pH of the culture medium is reduced, a lower amount of neutralizing agent is necessary. The formation of lactate salt is correspondingly reduced and proportionally less regeneration of free acid is required in order to recovery lactic acid. The recovery process may employ any of the known methods (T. B. Vickroy, Volume 3, Chapter 38 of "Comprehensive Biotechnology," (editor: M. Moo-Young), Pergamon, Oxford, 1985.)(R. Datta et al., FEMS Microbiology Reviews 16, 221–231, 1995). Typically, the microorganisms are removed by filtration or centrifugation prior to lactic acid recovery. Known methods for lactic acid recovery include, for instance, the extraction of lactic acid into an immiscible solvent phase or the distillation of lactic acid or an ester thereof. Higher yields with respect to the carbon source (g of lactic acid/g of glucose consumed) and higher productivities (g of lactic acid/l/h) are obtained by growing yeast strains, particularly *Saccharomyces* strains, in media lacking $Mg^{++}$ and $Zn^{++}$ ions or having a reduced availability of said ions. Preferably, culture media will contain less than 5 mM of $Mg^{++}$, and/or less than 0.02 mM of $Zn^{++}$.

The present invention offers the following advantages in the production of lactic acid:

1. When the fermentation is carried out at pH 4.5 or less, there is less danger of contamination by foreign microorganisms, as compared with the conventional process. Further, the fermentation facility can be simplified and the fermentation control can be facilitated.
2. Since less neutralizing agent is added to the culture medium for neutralization, there is correspondingly less need to use mineral acids or other regenerating agents for conversion of the lactate salt to free lactic acid. Therefore, the production cost can be reduced.
3. Since less neutralizing agent is added to the culture medium, the viscosity of the culture broth is reduced. Consequently, the broth is easier to process.
4. The cells separated in accordance with the present invention can be utilized again as seed microorganisms for a fresh lactic acid fermentation.
5. The cells can be continuously separated and recovered during the lactic acid fermentation, in accordance with the present invention, and hence, the fermentation can be carried out continuously.
6. Since the recombinant yeast strains lack ethanol production ability and pyruvate dehydrogenase activity or have both a reduced ethanol production and a reduced pyruvate dehydrogenase activity, the production of lactic acid can be carried out with higher yield in comparison to yeast strains having both a wild-type ability to produce ethanol and a wild-type ability for the utilization of pyruvate by the mitochondria.
7. The production of lactic acid by metabolically engineered non-conventional yeasts belonging to the *Kluyveromyces*, *Torulaspora* and *Zygosaccharomyces* species can be obtained from non conventional carbon sources (i.e., galactose-lactose-sucrose-raffinose-maltose-cellobiose-arabinose-xylose, to give some examples), growing the cells in high-sugar medium and growing the cells in presence of high concentration of lactic acid.

Key enzymatic reactions at the pyruvate branch-point are catalysed by the following enzymes: (1): pyruvate decarboxylase; (2): alcohol dehydrogenase; (3): acetaldehyde dehydrogenase;(4): acetyl-CoA synthetase; (5): acetyl-CoA shuttle from the cytosol to mitochondria;(6): acetyl-CoA shuttle from mitochondria to the cytosol; (7): heterologous lactate dehydrogenase. (8): pyruvate dehydrogenase. Enzymatic reactions involved in anaplerotic syntheses have been omitted.

Figure 1:
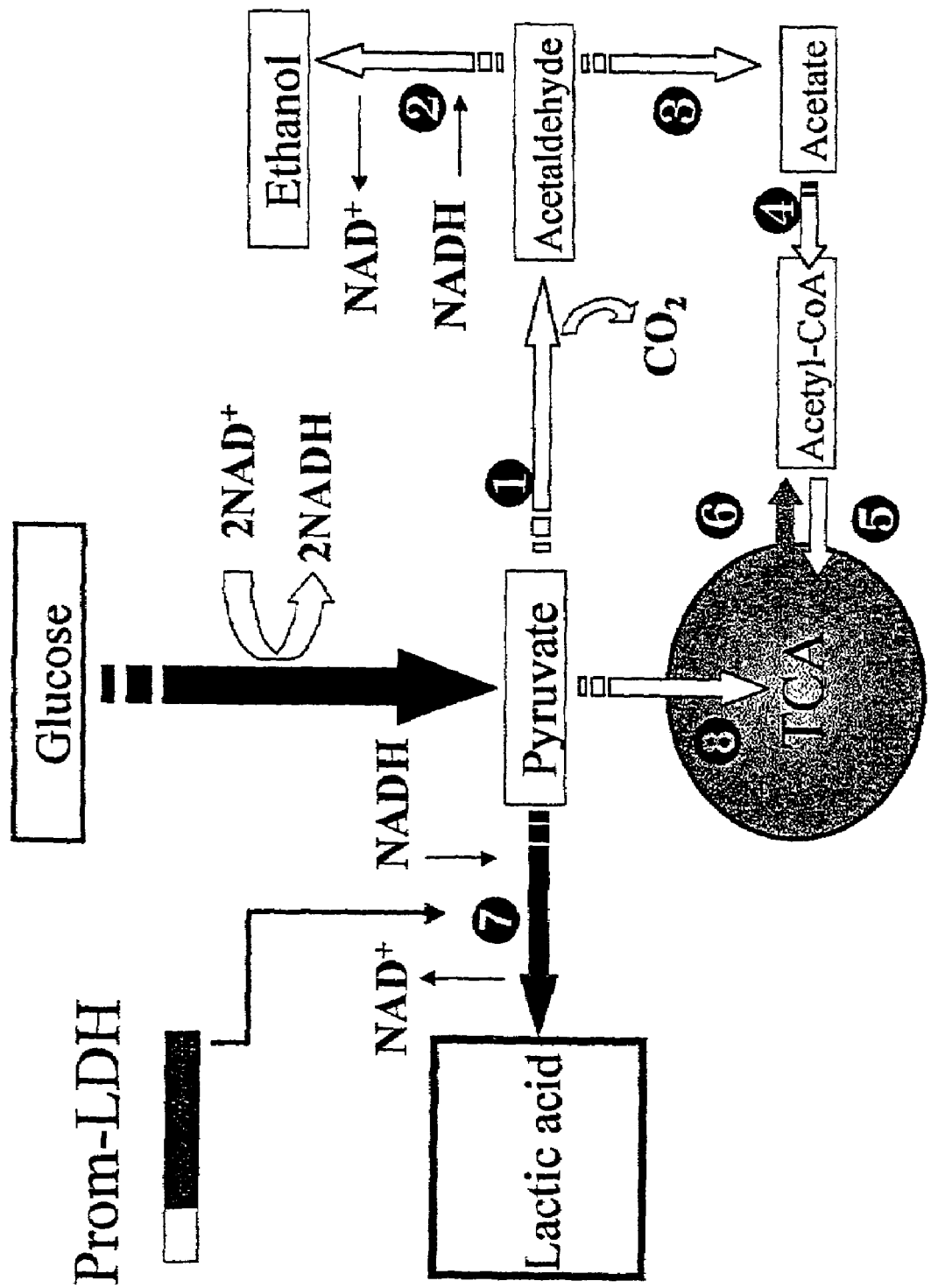
FIG. 1. Cloning of the lactate dehydrogenase gene shifts the glycolytic flux towards the production of lactic acid.
Figure 2:
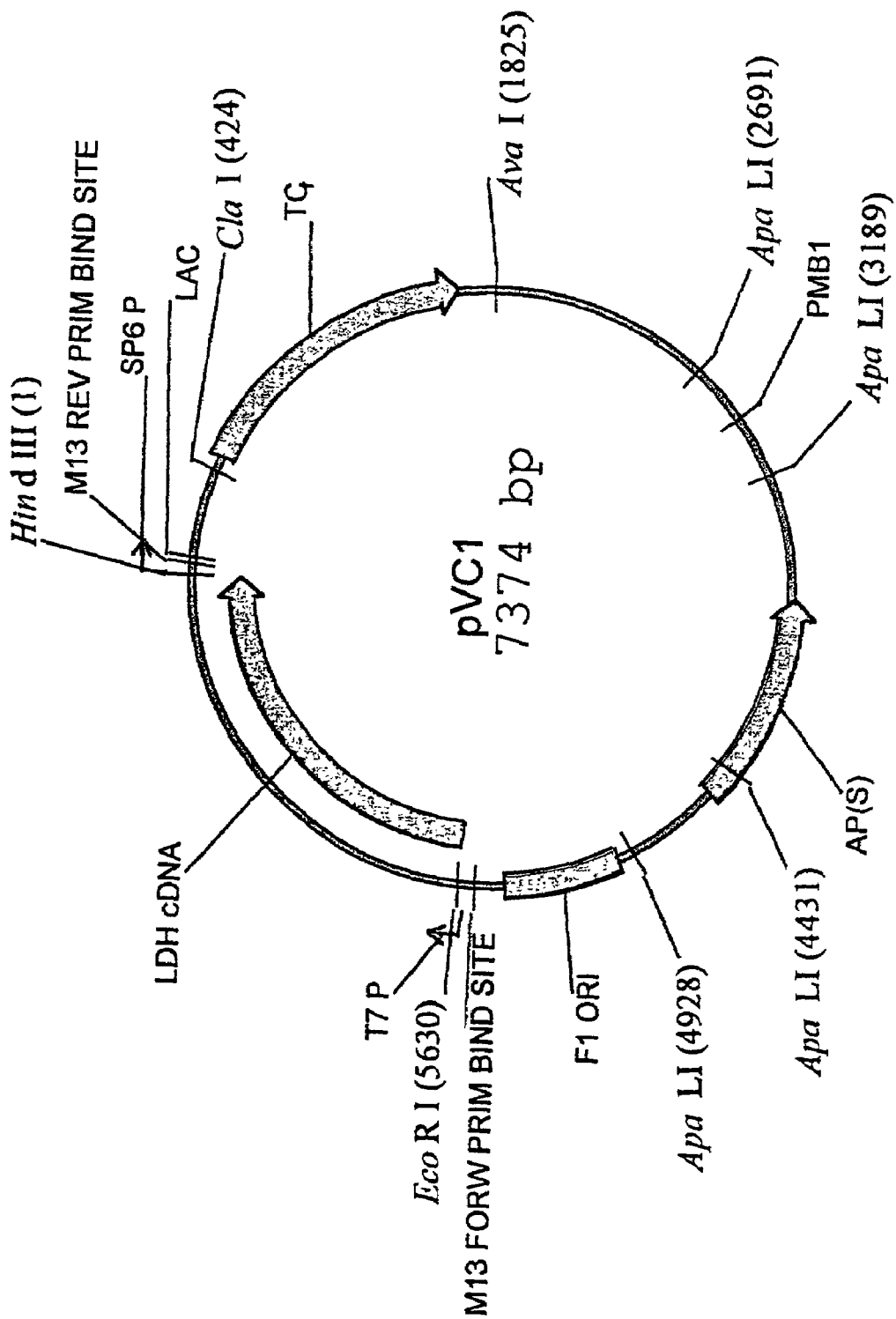

FIG. 2. Diagram of the plasmid pVC1.

Figure 3A:
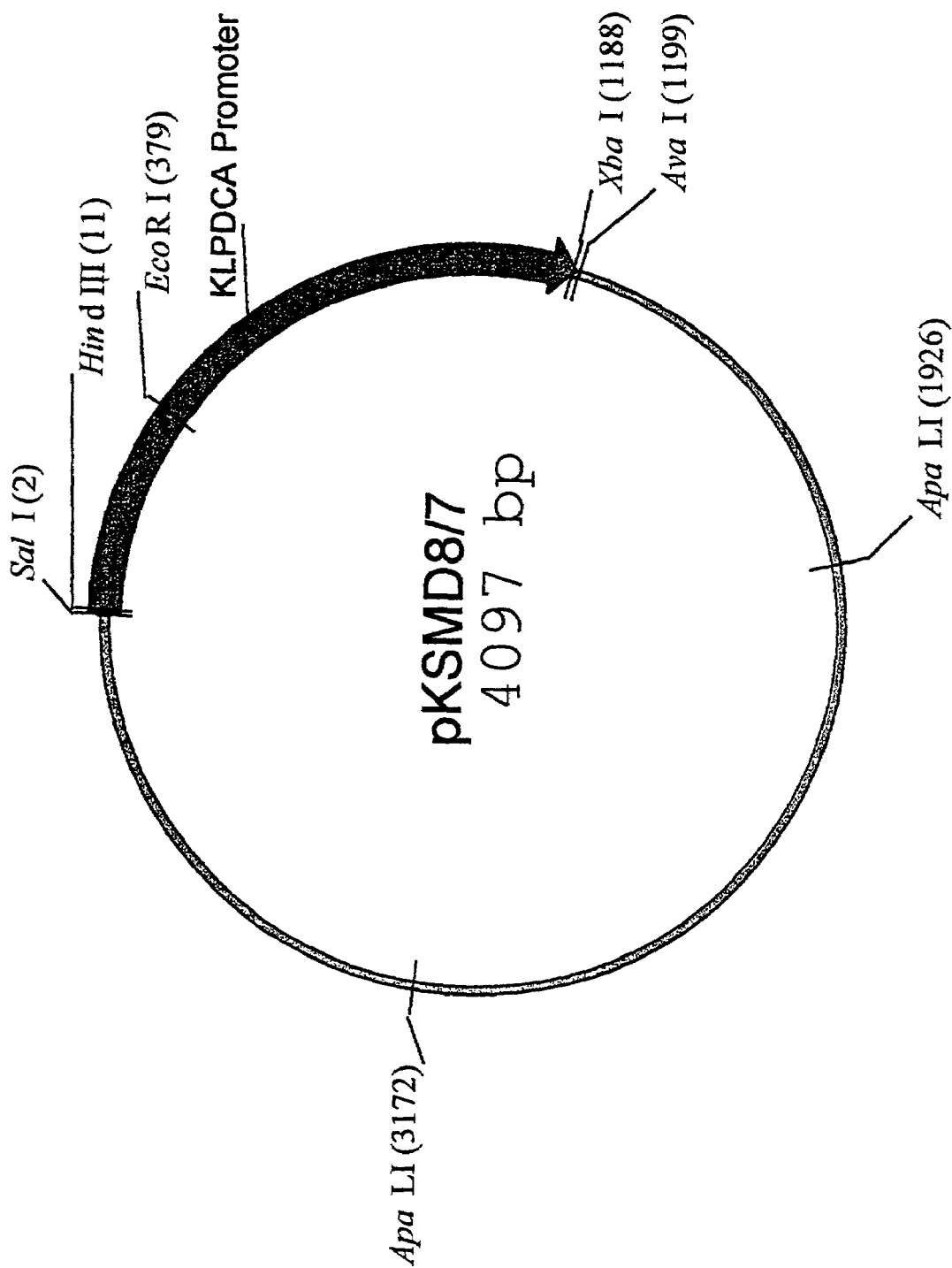

FIG. 3A., 3B. Diagram of the plasmid pKSMD8/7 and pKSEXH/16, respectively.

Figure 4:
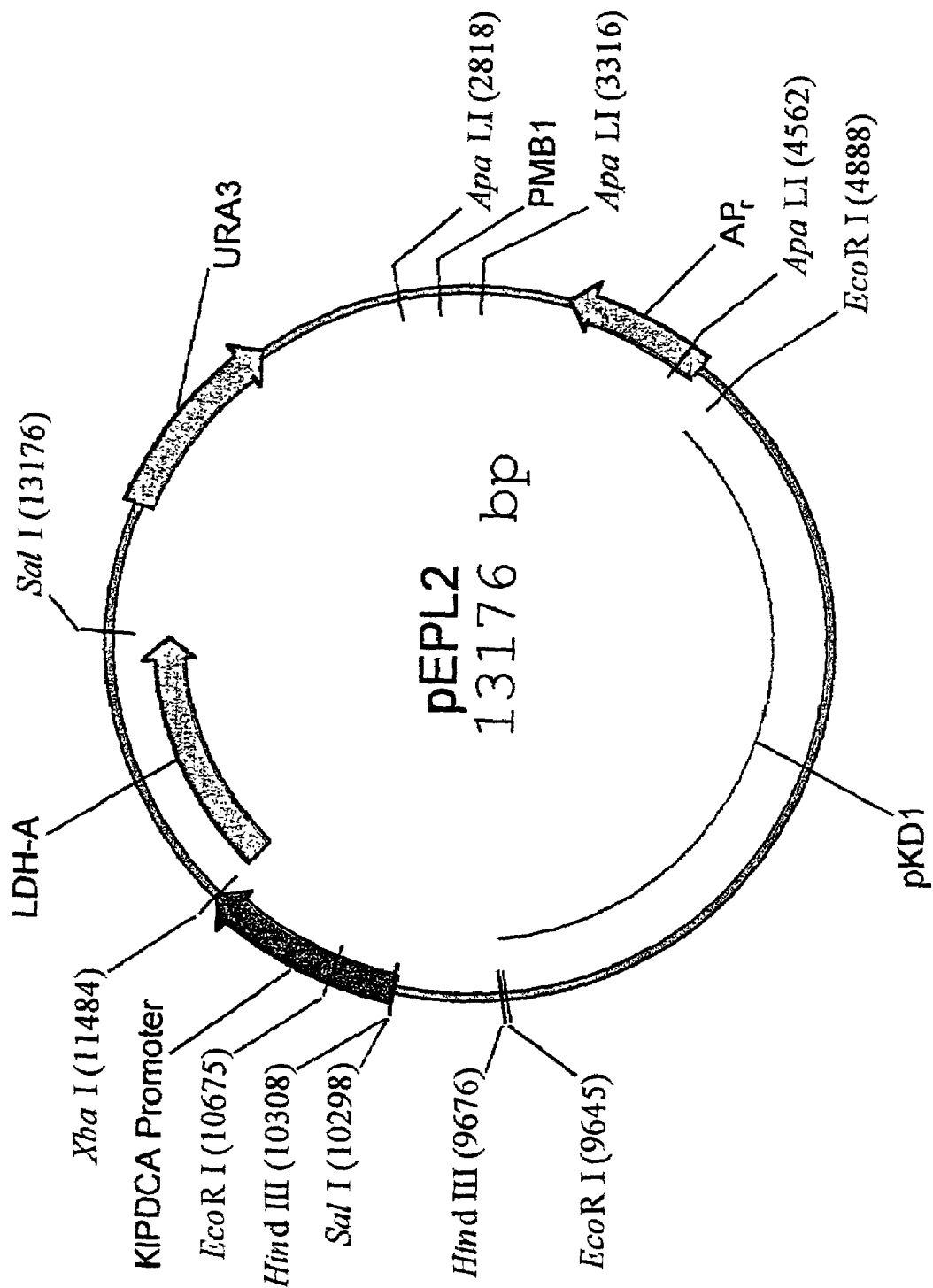

FIG. 4. Diagram of the plasmid pEPL2.

Figure 5:
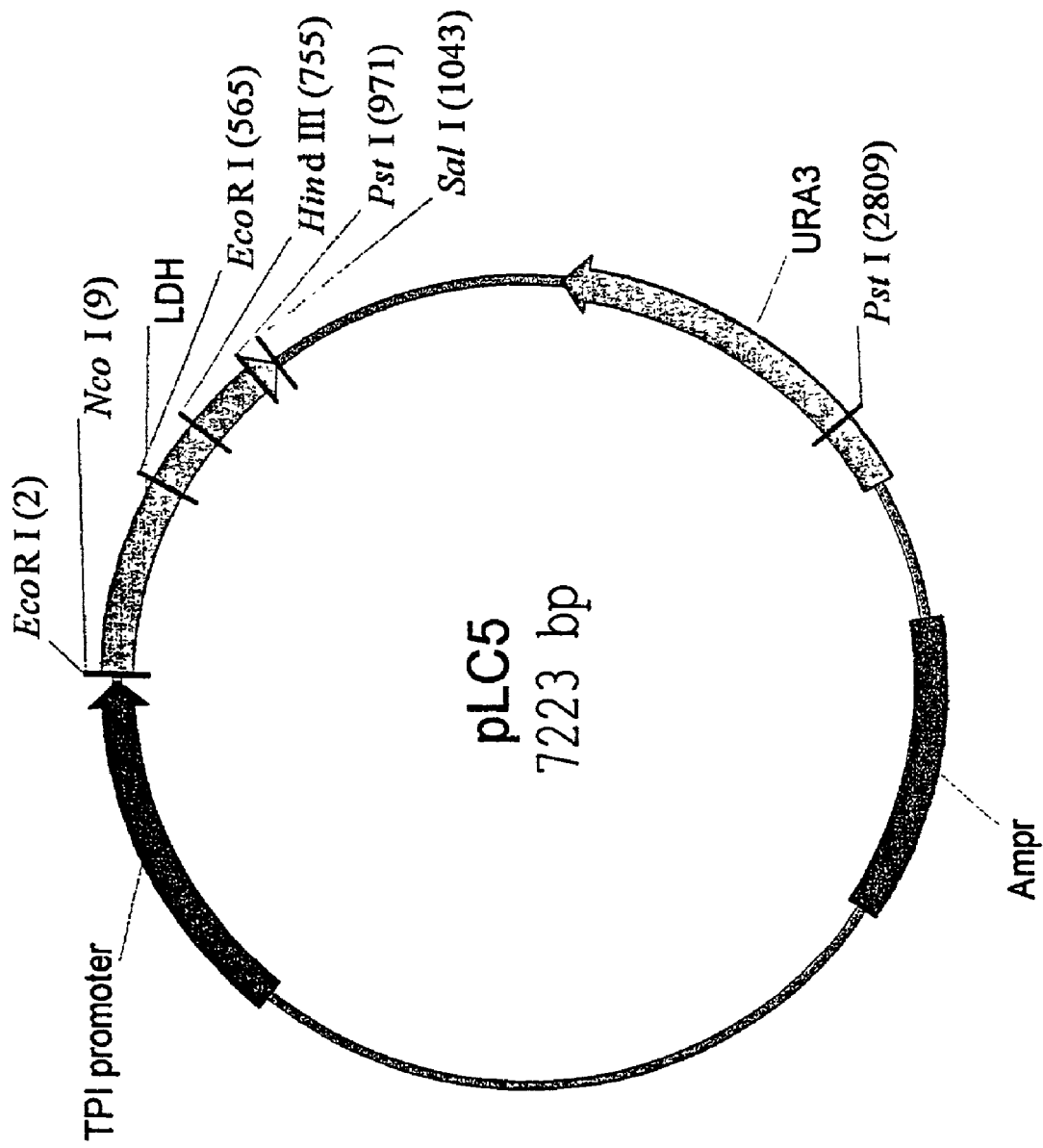

FIG. 5. Diagram of the plasmid pLC5.

Figure 6:
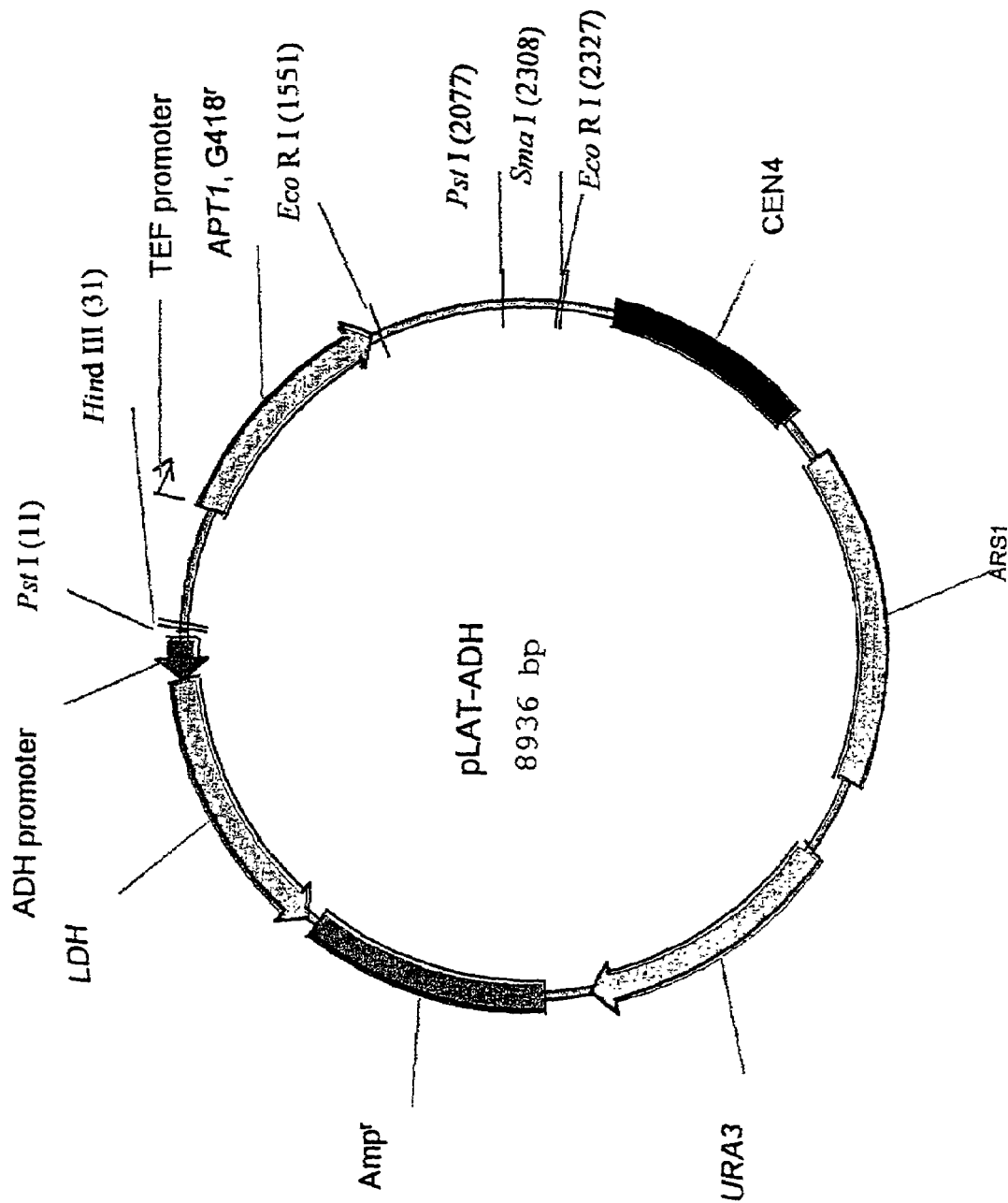

FIG. 6. Diagram of the plasmid pLAT-ADH.

FIG. 7A. L(+)-Lactic acid production from the transformed *Kluyveromyces lactis* PM6-7a[pEPL2] during growth on Glu-YNB based media. The residual glucose concentration at T=49 was not detectable. Production of D(−)-lactic acid was not detectable too. The LDH specific activity was higher than 3 U/mg of total cell protein along all the experiment.

Similar results have been obtained using the bacterial *L. casei* LDH (data not shown).

(▲) cells/ml; (−) pH value; (○) Ethanol production, g/l
(■) L(+)-Lactic acid production, g/l FIG. 7B. L(+)-Lactic acid production from the transformed *Kluyveromyces lactis* PM6-7a[pEPL2] during growth on Glu-YNB based media. Medium was buffered at time T=0 (pH=5.6) using 200 mM phosphate buffer. In this text batch, the pH value decreases much later than during the text batch shown in FIG. 7A. The residual glucose concentration at T=49 was not detectable. The LDH specific activity was higher than 3 U/mg of total cell protein along all the experiment.

Similar results have been obtained using the bacterial *L. casei* LDH (data not shown).

(▲) cells/ml; (−) pH value; (○) Ethanol production, g/l
(■) L(+)-Lactic acid production, g/l FIG. 8A. L(+)-Lactic acid production from the transformed *Kluyveromyces lactis* PM1/C1[pEPL2] during growth on Glu-YNB based media. The residual glucose concentration at T=60 was 12,01 g/l. Longer incubation times did not yield higher productions of both biomass and L(+)-Lactic acid. The LDH specific activity was higher than 3 U/mg of total cell protein along all the experiment.

Similar results have been obtained using the bacterial *L. casei* LDH (data not shown).

(▲) cells/ml; (−) pH value; (○) Ethanol production, g/l
(■) L(+)-Lactic acid production, g/l FIG. 8B. L(+)-Lactic acid production from the transformed *Kluyveromyces lactis* PM1/C1[pEPL2] during growth on Glu-YNB based media. Medium was buffered at time T=0 (pH=5.6) using 200 mM phosphate buffer In this text batch, the pH value decreases much later than during the text batch shown in FIG. 8A. The residual glucose concentration at T=87 was zero. The LDH specific activity was higher than 3 U/mg of total cell protein along all the experiment.

(▲) cells/ml; (-) pH value; (○) Ethanol production, g/l
(■) L(+)-Lactic acid production, g/l Similar results have been obtained using the bacterial *L. casei* LDH (data not shown).

FIG. 9A. L(+)-Lactic acid production from the transformed *Kluyveromyces* BM3-12D[pLAZ10] cells in stirred tank bioreactor (see also text)
(▲) cells/ml; (○) Glucose concentration, g/l
(■) L(+)-Lactic acid production, g/l FIG. 9B. L(+)-Lactic acid yield from the transformed *Kluyveromyces* BM3-12D[pLAZ10] cells in stirred tank bioreactor.

Glucose Vs lactic acid production. The yield (g/g) is 85.46%.

Figure 10:
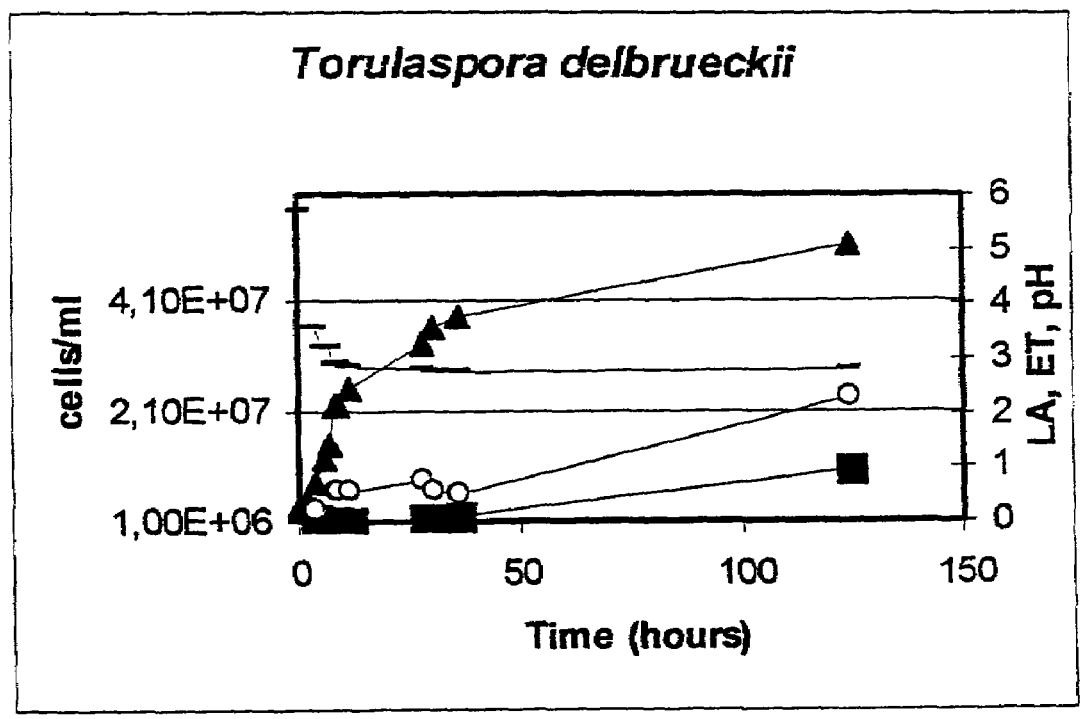

FIG. 10. L(+)-Lactic acid production from the transformed *Torulaspora* (syn. *Zygosaccharomyces*) *delbrueckii* CBS817[pLAT-ADH] during growth on Glu-YNB based media. The residual glucose concentration at T=130 was 3 g/l. Longer incubation times did not yield higher productions of both biomass and L(+)-Lactic acid. The LDH specific activity was higher than 0.5 U/mg of total cell protein along all the experiment.

(▲) cells/ml; (-) pH value; (○) Ethanol production, g/l
(■) L(+)-Lactic acid production, g/l FIG. 11. L(+)-Lactic acid production from the transformed *Zygosaccharomyces bailii* ATCC60483[PLAT-ADH] during growth on Glu-YNB based media. The residual glucose concentration at T=60 was 8 g/l. Longer incubation times did not yield higher productions of both biomass and L(+)-Lactic acid. The LDH specific activity was higher than 0.5 U/mg of total cell protein along all the experiment. Similar results were obtained using a different strain (ATCC36947, data not shown)

(▲) cells/ml; (-) pH value; (○) Ethanol production, g/l
(■) L(+)-Lactic acid production, g/l

DETAILED DESCRIPTION OF THE INVENTION

Definitions

The following definitions are provided in order to aid those skilled in the art in understanding the detailed description of the present invention.

"Amplification" refers to increasing the number of copies of a desired nucleic acid molecule.

"Codon" refers to a sequence of three nucleotides that specify a particular amino acid.

"Deletion" refers to a mutation removing one or more nucleotides from a nucleic acid sequence.

"DNA ligase" refers to an enzyme that covalently joins two pieces of double-stranded DNA.

"Electroporation" refers to a method of introducing foreign DNA into cells that uses a brief, high voltage dc charge to permeabilize the host cells, causing them to take up extra-chromosomal DNA.

The term "endogenous" refers to materials originating from within the organism or cell.

"Endonuclease" refers to an enzyme that hydrolyzes double stranded DNA at internal locations.

The term "expression" refers to the transcription of a gene to produce the corresponding mRNA and translation of this mRNA to produce the corresponding gene product, i.e., a peptide, polypeptide, or protein.

The term "expression of antisense RNA" refers to the transcription of a DNA to produce a first RNA molecule capable of hybridizing to a second RNA molecule encoding a gene product, e.g. a protein. Formation of the RNA-RNA hybrid inhibits translation of the second RNA molecule to produce the gene product.

The phrase "functionally linked" refers to a promoter or promoter region and a coding or structural sequence in such an orientation and distance that transcription of the coding or structural sequence may be directed by the promoter or promoter region.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "genome" encompasses both the chromosome and plasmids within a host cell. Encoding DNAs of the present invention introduced into host cells can therefore be either chromosomally-integrated or plasmid-localized.

"Heterologous DNA" refers to DNA from a source different than that of the recipient cell.

"Homologous DNA" refers to DNA from the same source as that of the recipient cell.

"Hybridization" refers to the ability of a strand of nucleic acid to join with a complementary strand via base pairing. Hybridization occurs when complementary sequences in the two nucleic acid strands bind to one another.

"Lactate dehydrogenase" (LDH) refers to a protein that catalyzes the conversion of pyruvate and NADH to lactic acid and $NAD^+$. L(+)-LDH produces L(+)-lactic acid; D(-)-LDH produces D(-)-lactic acid.

The term "lactate transporter" refers to a protein that allows the transport of lactate from inside to outside the cell.

"Mutation" refers to any change or alteration in a nucleic acid sequence. Several types exist, including point, frame shift, and splicing. Mutation may be performed specifically (e.g. site directed mutagenesis) or randomly (e.g. via chemical agents, passage through repair minus bacterial strains).

Nucleic acid codes: A=adenosine; C=cytosine; G=guanosine; T=thymidine; N=equimolar A, C, G, and T; I=deoxyinosine; K=equimolar G and T; R=equimolar A and G; S=equimolar C and G; W=equimolar A and T; Y=equimolar C and T.

"Open reading frame (ORF)" refers to a region of DNA or RNA encoding a peptide, polypeptide, or protein.

"Pyruvate decarboxylase" (PDC) refers to a protein which catalyzes the conversion of pyruvate to acetaldehyde.

"Pyruvate dehydrogenase" (PDH) refers to a protein complex which catalyzes the conversion of pyruvate to acetyl-CoA.

"Plasmid" refers to a circular, extrachromosomal, self-replicating piece of DNA.

"Point mutation" refers to an alteration of a single nucleotide in a nucleic acid sequence.

"Polymerase chain reaction (PCR)" refers to an enzymatic technique to create multiple copies of one sequence of nucleic acid. Copies of DNA sequence are prepared by shuttling a DNA polymerase between two amplimers. The basis of this amplification method is multiple cycles of temperature changes to denature, then re-anneal amplimers, followed by extension to synthesize new DNA strands in the region located between the flanking amplimers.

The term "promoter" or "promoter region" refers to a DNA sequence, that includes elements controlling the production of messenger RNA (mRNA) by providing the recognition site for RNA polymerase and/or other factors necessary for start of transcription at the correct site.

A "recombinant cell" or "transformed cell" is a cell whose DNA has been altered by the introduction of an exogenous nucleic acid molecule into that cell.

The term "recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed. Recombinant DNA constructs or recombinant vectors may alternatively be constructed to be capable of expressing antisense RNAs, in order to inhibit translation of a specific RNA of interest.

"Reduced (enzymatic) activity" refers to lower measured enzymatic activity isolated from a transformed or mutagenized strain as compared to the measured enzymatic activity isolated from a wild type strain of the same species. Reduced enzymatic activity may be the result of lowered concentrations of the enzyme, lowered specific activity of the enzyme, or a combination thereof.

"Repair minus" or "repair deficient" strains refer to organisms having reduced or eliminated DNA repair pathways. Such strains demonstrate increased mutation rates as compared to the rates of wild type strains of the same species. Propagation of a nucleic acid sequence through a repair minus strain results in the incorporation of random mutations throughout the nucleic acid sequence.

"Restriction enzyme" refers to an enzyme that recognizes a specific palindromic sequence of nucleotides in double stranded DNA and cleaves both strands; also called a restriction endonuclease. Cleavage typically occurs within the restriction site.

"Selectable marker" refers to a nucleic acid sequence whose expression confers a phenotype facilitating identification of cells containing the nucleic acid sequence. Selectable markers include those which confer resistance to toxic chemicals (e.g. ampicillin resistance, kanamycin resistance), complement a nutritional deficiency (e.g. uracil, histidine, leucine), or impart a visually distinguishing characteristic (e.g. color changes, fluorescence).

"Transcription" refers to the process of producing an RNA copy from a DNA template.

"Transformation" refers to a process of introducing an exogenous nucleic acid sequence (e.g., a vector, plasmid, recombinant nucleic acid molecule) into a cell in which that exogenous nucleic acid is incorporated into a chromosome or is capable of autonomous replication.

"Translation" refers to the production of protein from messenger RNA.

The term "yield" refers to the amount of lactic acid produced (gr/l) divided by the amount of glucose consumed (gr/l).

"Unit" of enzyme refers to the enzymatic activity and indicates the amount of micromoles of substrate converted per mg of total cell proteins per minute.

"Vector" refers to a plasmid, cosmid, bacteriophage, or virus that carries nucleic acid sequences into a host organism.

Site-directed Mutagenesis of the Bovine Lactate Dehydrogenase Gene (LDH-A)

In order to isolate from the full length cDNA the coding sequence of the bovine enzyme LDH-A (EC 1.1.1.27), a classical site directed mutagenesis, (J. Biol. Chem. 253: 6551, 1978, Meth. Enzymol. 154:329, 1987), was performed. Oligonucleotides-driven site-specific mutagenesis is based on the in vitro hybridization of a single strand DNA fragment with a synthetic oligonucleotide, which is complementary to the DNA fragment except for a central mismatching region in correspondence of the DNA sequence that must to be mutagenized.

In order to introduce a Xba I restriction enzyme site 11 bp before the ATG codon, the 1743 bp bovine LDH cDNA was cloned from the plasmid pLDH12 (Ishiguro et al., Gene, 91 281–285, 1991) by digestion with Eco RI and Hind III restriction enzymes (New England Biolabs, Beverly, Mass.). The isolated DNA fragment was then inserted in the pAL-TER-1 (Promega, cat # 96210; lot # 48645, 1996) expression vector.

Such vector contains M13 and R408 bacteriophages origin of replication and two genes for antibiotic resistance. One of these genes, for tetracycline resistance, is functional. The other (i.e., ampicillin resistance) has been inactivated. An oligonucleotide is provided which restores ampicillin resistance to the mutant strand during mutagenesis reaction (oligoAMP; Promega, Madison,. Wis. Tab. 1). This oligonucleotide is annealed to the single-stranded DNA (ssDNA) template. At the same time the mutagenic oligonucleotide (oligoLDH, Madison Wis.) has been annealed as well. Following DNA synthesis and ligation, the DNA is transformed into a repair minus strain of $E.\ coli$ (BMH 71-18 muts; kit Promega). Selection was performed on LB+ampicillin (Molecular Cloning a laboratory manual, edited by Sambrook et al., Cold Spring Harbor Laboratory Press). A second round of transformation in JM 109 (kit Promega) $E.\ coli$ strain ensured proper segregation of mutant and wild type plasmids.

| OLIGONUCLEOTIDES | SEQUENCE | |
|---|---|---|
| OligoAMP | 5'-GTTGCCATTGCTGCAGGCATCGTGGTG-3' | (Sequence Id. No. 1) |
| OligoLDH | 5'-CCTTTAGGG<u>TCTAGA</u>TCCAAGATGGCAAC-3' | (Sequence Id. No. 2) |

Table 1: Nucleotide sequence of the synthetic oligonucleotides used for the site-directed mutagenesis. The underlined sequence in the oligoLDH show the Xba I restriction site introduced by mutagenesis.

Further details of the technique and material used (with the exception of the oligoLDH) can be found in the kit datasheet.

The plasmid obtained, containing the mutated CDNA for the bovine LDH, was denominated pVC1 (FIG. 2).

PCR Mutagenesis of the Bacterial Lactate Dehydrogenase Gene (LDH) from *Lactobacillus casei*, *Bacillus megaterium* and *Bacillus stearothermophylus*.

The original starting codon (GTG) of the *Lactobacillus casei* LDH gene (GTG) (the LDH sequence is available at the accession no. M76708 of the GenBank Sequence Database) is not correctly recognised by *S. cerevisiae*. We obtained plasmid pST2 and LDH sequence from Hutkins Robert, University of Nebraska, USA). pST2 is based on pUC19 vector (Boebringer Mannheim GmbH, Mannheim, Germany, cat. 885827) and contains a BamHI-SphI LDH-cDNA fragment amplified from the *L. casei* 686 (Culture collection of the University of Nebraska).

In order to obtain a coding sequence starting with the usual eukaryotic first codon (i.e. ATG), the LDH sequence has been mutagenised via PCR.

The introduction of a Nco I restriction enzyme site at position 163 of the LDH sequence (accession n. M76708 of the GenBAnk Sequence Database, supra), allows the concomitant change of the original GTG codon into ATG. PCR reaction (Mastercycler 5330, Eppendorf, Hamburg, Germany) was performed starting from the plasmid pLC1, based on pGEM7Z f(+) (Promega corporation, Madison Wis., USA, cat.P2251) vector, and containing the *L.casei*'s gene (fragment BamHI-SphI excided from pST2). The sequences of the oligonucleotides used as primers of the reaction are reported in Table 2.

| | | |
|---|---|---|
| Amplification cycles: 94°; 1' | | (denaturating step) |
| 94° 30" | | (denaturating step) |
| 56° 30" | 4 times | (primer annealing step) |
| 68° 3' | | (extension step) |
| 94° 30" | | (denaturating step) |
| 60° 30" | 23 times | (primer annealing step) |
| 68° 3' | | (extension step) |
| 68° 3' | | (final extension step) |

At the end of the reaction, a single band, corresponding to the amplified and mutated gene, was isolated. The DNA fragment was then inserted at the EcoRV site of pMOSBlue (Amersham Life Science, Buckingamshire, England; cod. RPN5110) cloning vector with a blunt-end ligation, giving rise to pLC3 plasmid.

Any other mutagenesis's protocol can be analogously used.

Construction of the PEPL2 Replicative Vector Containing the KLPDCA Promoter and the Bovine LDH cDNA.

Figure 3B:
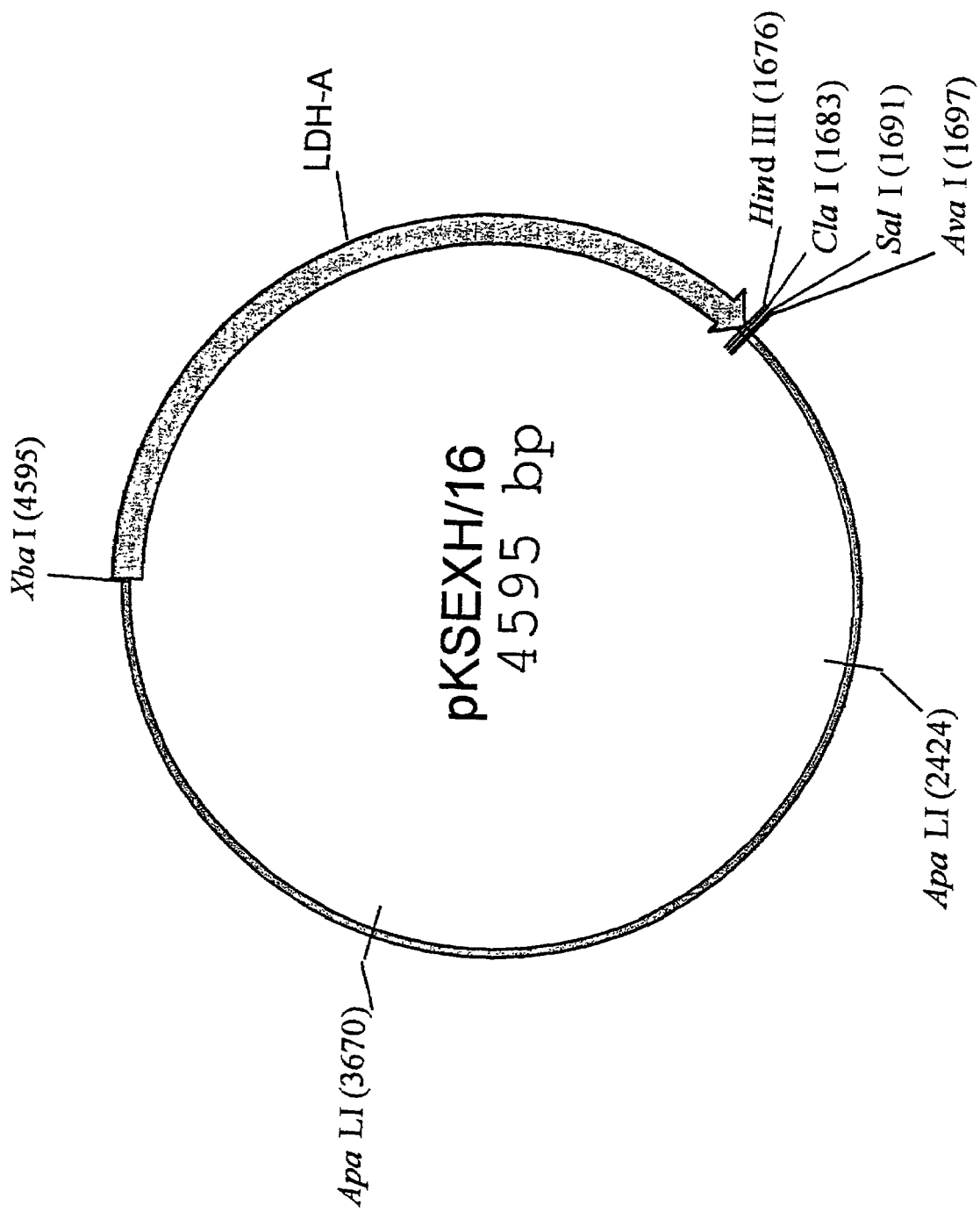

The KlPDCA promoter and the coding sequence were subcloned as a 4 Kbp HindIII fragment from a *K. lactis* genomic library clone complementing the rag 6 mutation of *K. lactis* (Bianchi et al., Mol. Microbiol., 19: 27–36, 1996). The promoter region was subcloned into Sal I and Xba I sites of the vector pBleuscript II KS (Stratagene, LaJolla, Calif. # 212205) with T4 DNA ligase using molecular cloning standard procedure (Sambrook et al., Molecular Cloning, surra). The bovine LDH sequence, isolated as a Xba I-Hind III fragment of 1675 bp from the pVC1 vector, was cloned in the corresponding cloning sites of the vector pBleuscript II KS. GM82 *E. coli* strain (dam⁻dcm⁻)(available from ATCC or CGSC collections) was transformed with the two new vectors, called respectively pKSMD8/7 and pKSEXH/16 (FIGS. 3A and 3B).

KlPDCA promoter and bovine LDH sequence, isolated as Sal I-Xba I fragments, respectively from pKSMD8/7 and pKSEXH/16, were ligated in vitro with T4 DNA ligase at room temperature in the presence of Sal I endonuclease in order to allow the ligation at Xba I ends. The ligation product was cloned in Sal I cloning site of pE1 vector (Bianchi M.et al., Curr. Genet. 12: 185–192, 1987; Chen X. J. et al., Curr. Genet. 16: 95–98, 1989 and U.S. Pat. No. 5,166,070). This plasmid is based on the YIp5 integrative plasmid containing the *Saccharomyces cerevisiae* genetic marker URA3 and on the pKD1 plasmid (U.S. Pat. No. 5,166,070), isolated from *Kluyveromyces drosophilarum*. The plasmid pE1 has a functional organization similar to the *S. cerevisiae* 2μ DNA and is able to replicate in a stable way in *Kluyveromyces lactis* cells (Chen X. J. et al., supra). The URA3 marker on the plasmid allows the complementation of the *K. lactis* uraA1-1 mutation (de Louvencourt et al., J. Bacteriol. 154: 737–742 (1982)), and therefore growth of transformed cells in selective medium without uracil.

The vector obtained was called pEPL2 (FIG. 4) and used to transform *E. coli* DH5-alfa strain (Life Technologies Inc., Gaitherburg, Mass.).

Construction of the pEPL4 Replicative Vector Containing the KlPDCA Promoter and the Bacterial LDH Gene.

TABLE 2

| OLIGONUCLEOTIDES | SEQUENCE | |
|---|---|---|
| OligoATG | 5'-<u>CCATGG</u>CAAGTATTACGGATAAGGATC-3' | (Sequence Id. No. 3) |
| OligoANTISENSE | 5'-CTATCACTGCAGGGTTTCGATGTC-3' | (Sequence Id. No. 4) |

Table 2: Nucleotide sequence of the synthetic oligonucleotides used for the PCR amplification. The underlined sequences in the oligoATG shows the NcoI restriction site introduced by mutagenesis, and the resulting ATG starting codon obtained.

Following a classical PCR approach we also cloned the L(+) LDH genes from the bacteria *Bacillus megaterium* and *Bacillus stearothermophylus* (Biol. Chem. Hoppe-Seyler, 1987, 368:1391) (Biol. Chem. Hoppe-Seyler, 1987, 368: 1167) (the DNA sequence is also available at the accession nos. M22305 and M19396 of the Genbank Sequence Database) in expression vectors for yeasts *S. cerevisiae* (i.e., pBME2 and pBST2, respectively, see below).

The bovine LDH gene described for the pEPL2 plasmid was substituted with the LDH DNA sequence from the bacterial *Lactobacillus casei* gene (see above), following classical molecular approaches described throughout the text, yielding the plasmid pEPL4. Transformed *K. lactis* yeast cells bearing the bovine or bacterial LDHs gave similar results.

Construction of the PLAZ10 Replicative Vector Containing the KlPDCA Promoter and the Bovine LDH cDNA.

Vector pLAZ10 was obtained by cloning the SalI fragment of pEPL2, bearing the KlPDC1 promoter and the bovine LDH coding sequence, into the unique SalI site of vector p3K31. Vector p3K31 is composed of the commercial vector pUC19 and the G418 resistance cassette of vector pKan707 (Fleer et al. Bio/technology 9: 968–974, 1991) inserted in the unique SphI site of plasmid pKD1.

Construction of the PLC5, PLC7, PB1, pBM2, PBST2, pLC5-KanMX and pJEN1 Integrative Vectors.

The *L. casei* LDH gene, was excised from pLC3 (described above) with a NcoI-SalI digestion, and ligated into pYX012 or pYX022 integrative vectors (R&D System Europe Ltd, Abingdon, England).

The two plasmids obtained, containing the mutated DNA for the bacterial LDH gene under the control of the TPI promoter, and carrying the auxotrophic markers URA3 or HIS3, were denominated respectively pLC5 (FIG. 5) and pLC7. For the construction of pB1, pBM2 and pBST2 we used an approach similar to that described for the construction of pLC5; however, we used the bovine LDH, the *B. megaterium* LDH and the *B. stearothermophylus* LDH (Biol. Chem. Hoppe-Seyler, 1987, 368: 1391)(Biol. Chem. Hoppe-Seyler, 1987, 368: 1167), respectively. Finally, plasmid pFA6a-KanMX (Wach et al, Yeast, 1994, 10:1793–1808) was digested with SacI and SmaI and the resulting fragment was ligated into pLC5 cut with the same enzymes yielding the plasmid pLC5-kanMX. On the plasmids, the LDH gene is under the control of the TPI promoter.

The DNA sequence of JEN1 (the DNA sequence is available at the accession no. U24155 of the Genbank Sequence Database), encoding for the lactate transporter of *S. cerevisiae* (Davis E. S., Thesis, 1994-Laboratory of Eukaryotic Gene Expression, Advanced Bioscience Laboratories) (Davis, E. S. et al., Proc. Natl. Acad. Sci. U.S.A. 89 (23), 11169, 1992) (Andre, B. Yeast (11), 1575, 1995), has been obtained from E. S. Davis (University of Maryland, USA). The JEN1 coding sequence has been amplified by classical PCR approach described throughout the text and cloned into the pasmid pYX022 (see above). On the integrative plasmid, JEN1 overexpression is under the control of the TPI promoter.

Construction of the pLAT-ADH Replicative Vector Containing the ADH1 Promoter and the Bovine LDH cDNA.

First, the pLDH-Kan plasmid was constructed, cloning at EcoRV site of the pBluescript II KS (Promega corporation, Madison Wis., USA, cat. 212208) cloning vector the APTI gene, conferring geneticin (G418) resistance, derived from a SmaI/EcoRV digestion of pFA6-KahMX4 vector (Wach et al. Yeast 10:1793–1808 (1994)).

Secondly, the coding region of bovine LDH gene was cloned under the control of *S. cerevisiae*'s ADH1 promoter and terminator sequences by subcloning a XbaI/HindIII fragment, from the previously described pVC1 plasmid into pVT102-U vector (Vernet et al. Gene 52:225–233 (1987)).

Finally, the whole expression cassette (ADH1 promoter—LDH gene—ADH1 terminator) was excided with a SphI digestion and ligated with pLDH-Kan, linearized with SphI, obtaining PLAT-ADH vector (FIG. 6)

Isolation of the *K. lactis* PMI/C1 Strain

Deletion of the KlPDCA gene in the PM6-7A yeast strain (MAT a, adeT-600, uraA1-1)(Wesolowski et al., Yeast 1992, 8: 711) yielded the strain PMI. Deletion has been carried out by insertion of the URA3 marker of *S. cerevisiae*. The strain PMI grows on glucose containing media; PDC activity is not detectable and the strain does not produce ethanol (Bianchi M. M., et al.,(1996), supra). It is important to underline that *S. cerevisiae* cells without any detectable PDC activity do not grow on glucose mineral media (Flikweert M. T. et al. Yeast, 12:247–257, 1996).

$1 \times 10^7$–$3 \times 10^7$ cells from a stationary culture of PMI yeast cells were plated on synthetic medium containing 5-fluoro-orotic acid. Growth of yeast cells in media containing 5-fluoroorotic acid allows the selection of cells impaired in uracile synthesis (McCusker and Davis, Yeast 7: 607–608 (1991)). After 5 days incubation at 28° C. some ura-mutants were isolated. One of these mutants obtained, called PMI/C1, resulted mutated in the URA3 gene previously introduced by integrative transformation, as it resulted from a complementation test by transformation with an URA3 gene-containing plasmid (Kep6 vector; Chen et al. . , J. Basic Microbiol. 28: 211–220 (1988)). The genotype of PMI/C1 is the following: MATa, adeT-600, uraA1-1, pdcA:: ura3.

Isolation of the CENPK113ΔPDC1 ΔPDC5ΔPDC6 CERPK113ΔPDC2 and GRF18UΔPDC2 Strain

The general strategy was to generate first single deletion mutants of each of the PDC genes (PDC1, PDC2, PDC5 and PDC6). The gene deletions were performed by integration of a loxP-Kan$^{SRD}$-loxP cassette by homologous recombination at the locus of the corresponding PDC gene using the short flanking homology (SFH) PCR method described by Wach et al. (1994; Yeast 10, 1793–1808) and Guldener et al. (1996; Nucleic Acids Res. 24, 2519–2524). Subsequently the deletion cassette was removed by expressing the cre-recombinase leading behind a single copy of the loxP site at the deletion locus. The pdc1 pdc5 pdc6 triple deletion mutant was created by subsequently crossing the single haploid deletion strains.

The PCR reaction was carried out on a DNA-template containing the gene for the kanamycin resistance (open reading frame of the *E. coli* transposon Tn903) fused to control sequences (promotor/terminator) of a certain *Schwanniomyces occidentalis* gene (confidential). This selection cassette is flanked on both ends by a loxp sequence (loxP-Kan$^{SRD}$-loxP) and was developed by SRD (Scientific Research and Development GmbH).The used primer to amplify the loxP-Kan$^{SRD}$-loxP cassette are designed so that the DNA sequence of the sense primer is homologous to the 5'-end of the selection cassette sequence and so that the primer presents in addition at its 5'-end a region 40 nucleotides, which corresponds to the 5'-terminal sequence of the certain *Saccharomyces cerevisiae* PDC gene. The antisense primer is constructed in an analogous manner, it is complementary to the 3'-end of the selection cassette, wherein this primer contains at its 5'-end a region of also preferably 40 nucleotides, which corresponds to the 3'-terminal sequence of the certain *Saccharomyces cerevisiae* PDC gene.

The following table shows the primers used for gene deletion of the corresponding PDC genes by SFH PCR method. Sequences underlined are homologue to the corresponding PDC gene and sequences complementary to the loxP-Kan$^{SRD}$-loxp cassette are in bold letters.

| | | |
|---|---|---|
| PDC1-S1 | <u>TTC TAC TCA TAA CCT CAC GCA AAA TAA CAC AGT CAA ATC ACA</u> GCT GAA GCT TCG TAC GC | (SEQ ID NO:5) |
| PDC1-S2 | <u>AAT GCT TAT AAA ACT TTA ACT AAT AAT TAG</u> | (SEQ ID NO:6) |

-continued

```
            AGA TTA AAT CGC ATA GGC CAC TAG TGG ATC TG

PDC5-S1     ATC AAT CTC AAA GAG AAC AAC ACA ATA CAA          (SEQ ID NO:7)
            TAA CAA GAA GCA GCT GAA GCT TCG TAC GC

PDC5-S2     AAA ATA CAC AAA CGT TGA ATC ATG AGT TTT          (SEQ ID NO:8)
            ATG TTA ATT AGC ATA GGC CAC TAG TGG ATC TG

PDC6-S1     TAA ATA AAA AAC CCA CGT AAT ATA GCA AAA          (SEQ ID NO:9)
            ACA TAT TGC CCA GCT GAA GCT TCG TAC GC

PDC6-S2     TTT ATT TGC AAC AAT AAT TCG TTT GAG TAC          (SEQ ID NO:10)
            ACT ACT AAT GGC ATA GGC CAC TAG TGG ATC TG

PDC2-S1     ACG CAA CTT GAA TTG GCA AAA TGG GCT TAT          (SEQ ID NO:11)
            GAG ACG TTC CCA GCT GAA GCT TCG TAC GC

PDC2-S2     AGC CTG TGT TAC CAG GTA AGT GTA AGT TAT          (SEQ ID NO:12)
            TAG AGT CTG GGC ATA GGC CAC TAG TGG ATC TG
```

The PCR amplified deletion cassette was used for the transformation of the prototrophic diploid *Saccharomyces cerevisiae* strain CEN.PK122 developed by SRD.

CEN.PK 122 (Mata, alpha, URA3, URA3, HIS3, HIS3, LEU2,
LEU2, TRP1, TRP1, MAL2-8$^c$, MAL2-8$^c$, SUC2, SUC2)

For selection of transformants, geneticin (G-418 sulfate, Life Technologies) was added at a final concentration of 200 mg/l. After tetrad analysis, G418 resistant spores were subsequently analyzed by diagnostic PCR to confirm the correct deletion of the corresponding PDC gene and to determine the mating type of the haploid strain.

To obtain a strain deleted for the three PDC genes, PDC1, PDC5 and PDC6, the haploid deletion strains were subsequently crossed. To obtain the two double deletion strains, pdc1::Kan$^{SRD}$pdc6::Kan$^{SRD}$ and pdc5::Kan$^{SRD}$pdc6::Kan$^{SRD}$, the corresponding haploid strains were crossed. After tetrad analysis, spores showing the non-parental ditype for the Kan$^{SRD}$ marker were subsequently analyzed by diagnostic PCR to confirm the correct deletion of both genes and to determine the mating type. The resulting double deletion strains were crossed to obtain the triple deletion strain. After tetrad analysis there was looked by diagnostic PCR for spores which are deleted for the three PDC genes.

To eliminate the Kan$^{SRD}$ marker from the successfully disrupted gene the haploid deletion strains (single, double and triple mutants) were transformed with the cre recombinase plasmid, pPK-ILV2$^{SMR}$ (developed by SRD). Plasmid pPK-ILV2$^{SMR}$ contains the cre-recombinase under the control of the GAL1 promoter and as dominant selection marker the ILV2 resistance gene, which allows yeast cells transformed with plasmid pPK-ILV2$^{SMR}$ to grow in the presence of sulfomethuron methyl (30 mg/l). Correct excision of the Kan$^{SRD}$ marker was subsequently analyzed by diagnostic PCR with whole yeast cells. To remove plasmid pPK-ILV2$^{SMR}$ the yeasts cells were incubated for an appropriate time without sulfomethuron methyl in the medium and subsequently searching for sulfomethuron methyl sensitive cells.

The following table shows the resulting yeast strains. The numbers in parentheses indicate the deleted nucleotides (ATG=1) of the corresponding genes. In the case of negative numbers means the first number the deleted nucleotides upstream of the ATG and the second number the deleted nucleotides downstream of the STOP codon.

TABLE

| Strain | Mating | | | | | | |
|---|---|---|---|---|---|---|---|
| CEN.PK184 | MATa | URA3 | HIS3 | LEU2 | TRP1 | $^c$ SUC2 | pdc1(-6, -2)::loxP |
| CEN.PK186 | MATa | URA3 | HIS3 | LEU2 | TRP1 | MAL2-8$^c$ SUC2 | pdc5(-6, -2)::loxP |
| CEN.PK210 | MATa | URA3 | HIS3 | LEU2 | TRP1 | MAL2-8$^c$ SUC2 | pdc6(-6, -2)::loxP |
| CEN.PK185 | MATa | URA3 | HIS3 | LEU2 | TRP1 | MAL2-8$^c$ SUC2 | pdc5(-6, -2)::loxP pdc6(-6, -2)::loxP |
| CEN.PK183 | MATa | URA3 | HIS3 | LEU2 | TRP1 | MAL2-8$^c$ SUC2 | pdc1(-6, -2)::loxP pdc6(-6, -2)::loxP |
| CEN.PK182 | MATa | URA3 | HIS3 | LEU2 | TRP1 | MAL2-8$^c$ SUC2 | pdc1(-6, -2)::loxP pdc5(-6, -2)::loxP pdc6(-6, -2)::loxP |
| CEN.PK211 | MATa | URA3 | HIS3 | LEU2 | TRP1 | MAL2-8$^c$ SUC2 | pdc2(101, 2730)::loxP |

Mainly we used the strains CEN.PK211 and CEN.PK182 which, in the tables summarizing the data obtained, are also named CENPK113ΔPDC2 and CENPK113ΔPDC1ΔPDC5ΔPDC6.

Using a similar approach a *S. cerevisiae* GRF18U strain (Mat alpha, his3, leu2, ura3) bearing a deletion in the PDC2 gene was build (GRF18UΔPDC2; Mat alpha, his3, leu2, ura3, pdc2::APT1). We used the APT1 gene, conferring G418 resistance, as a marker of the integration, isolated from the plasmid pFA6a-KanMX (Wach et al. supra); For the strain bearing deletions in the PDC1, PDC5 and PDC6 genes, the PDC activity is zero. For the strains bearing a deletion in the PDC2 gene, the PDC activity is about 20–40% of the level determined in the wild-type strains.

Isolation of the K. lactis BM3-12D [pLAZ10]

A double deletant strain Klpdc1Δ/Klpda1Δ was selected from the haploid segregant population of a diploid strain obtained by crossing strain MW341-5/Klpdc1Δ(MATα, lac4-8, leu2, lysA1-1, uraA1-1, Klpdc1::URA3; obtained as previously described in Bianchi et. al, 1996, Mol. Microbiol. 19 (1), 27–36, Destruelle et al., submitted) with strain CBS2359/Klpda1Δ(MATa, URA3-48, Klpda1::Tn5BLE) Deletion of the PDA1 gene, encoding for the pyruvate dehydrogenase complex E1-alpha subunit (EC.1.2.4.1) (the DNA sequence has been obtained by Steensma H. Y.; Faculty of Mathematics and Natural Sciences, Clusius Laboratory, Leiden, The Netherlands—the DNA sequence is also available at the accession no. AF023920 of the Genbank Sequence Database), in the yeast strain CBS2359 has been obtained following the classical PCR approach and yeast transformation described throughout the text. We used the marker Tn5B1e (Gatignol et al., Gene, 91:35, 1990) conferring phleomycin resistance, as a marker of the integration.

The double deletant strain, called BM1-3C (MATa, leu2, Klpdc1::URA3; Klpda1::Tn5BLE), was selected as a phleomycin resistant/antimycin sensitive segregant strain. The vector pLAZ10 was then genetically transferred to the double deletant strain as follows.

A pLAZ10 transformant of the Klpdc1::URA3 strain PMI/8 (MATa, adeT-600, uraA1-1, Klpdc1::URA3; Bianchi et al., Mol. Microbiol. 19:27–36. 1996) was crossed with strain MW109-8C (MATα, lysA1-1, trpA1-1). After sporulation of the resulting diploid strain, a geneticin resistant/antimycin sensitive strain, called strain 7C (MATα, adeT-600, lysA1-1, Klpdc1::URA3, pLAZ10$^+$), was selected.

Strain BM1-3C and strain 7C were crossed and phleomycin resistant/geneticin resistant haploid segregant strains were selected after sporulation of the obtained diploid strain. All of the haploid segregants were antimycin sensitive. The prototroph strain BM3-12D (Klpdc1::URA3; Klpda1:: Tn5BLE, pLAZ10$^+$) was chosen for further experiments.

Transformation of Kluyveromyces Yeast PM6-7A and PMI/C1 with the Vectors pEPL2 and pEPL4.

PM6-7A and PMI/C1 cells were grown in YPD medium until a concentration of $0.5 \times 10^8$ cells/ml, harvested, washed once in water, twice in 1M sorbitol, and resuspended in 1M sorbitol at a concentration of $2 \times 10^9$ cells/ml. Cells were electroporated (7.5 KV/cm, 25 μF, 200 Ω: GenePulser, Biorad, Hercules, Calif.) in the presence of 5–10 microg of pEPL2 or pEPL4. Selection of URA$^+$transformants was carried out in synthetic solid medium without uracil (0.7% w/v Yeast Nitrogen Base, 2 w/v % glucose, 200 mg/l adenine, 2 w/v % agar).

Transformation of Torulaspora Yeast with the Vector pLAT-ADH

CBS817 cells were grown in YPD medium until a concentration of $6 \times 10^7$ cells/ml, harvested, washed once in water, twice in 1M sorbitol, and resuspended in 1M sorbitol at a concentration of $2 \times 10^9$ cells/ml. Cells were electroporated (1.5 kV, 7.5 KV/cm, 25 μF, 200 Ω: GenePulser, Biorad, Hercules, Calif.) in the presence of 1 μg of pLAT-ADH.

Cells were grown overnight in sterile microbiological tubes containing 5 ml of YEPD, Sorbitol 1M. Selection of G418$^r$ transformants was carried out in solid medium (2 w/v % glucose, 2 w/v % Peptone, 1 w/v % Yeast extract, 2 w/v % agar, 200 μg/ml G418 (Gibco BRL, cat. 11811-031).

Transformation of Zygosaccharomyces Yeasts with the Vector pLAT-ADH.

ATTC36947 and ATTC60483 cells were grown in YPD medium until a concentration of $2 \times 10^8$ cells/ml, harvested, and resuspended at a concentration of $4 \times 10^8$ cells/ml in 0.1M lithium acetate, 10 mM dithiothreitol, 10 mM Tris-HCl, pH 7.5 at room temperature for one hour. The cells were washed once in water, twice in 1M sorbitol, and resuspended in 1M sorbitol at a concentration of $5 \times 10^9$ cells/ml. Cells were electroporated (1.5 kV, 7.5 KV/cm, 25 μF, 200 Ω: GenePulser, Biorad, Hercules, Calif.) in the presence of 3 μg of PLAT-ADH.

Cells were grown overnight in sterile microbiological tubes containing 5 ml of YEPD, Sorbitol 1M. Selection of G418$^r$ transformants was carried out in solid medium (2 w/v % glucose, 2 w/v % Peptone, 1 w/v % Yeast extract, 2 w/v % agar, 200 μg/ml G418 (Gibco BRL, cat. 11811-031).

Transformation of Saccharomyces Yeast cells with the Vectors PLC5, PLC7. pB1, pBST2, pBME2, pLAT-ADH, pLC5-kanMX and pJEN1

GRF18U (described above), GRF18UΔPDC2 (described above), GRF18U[pLC5] (Mat alpha, his3, leu2, ura3::TPI-LDH), CENPK113 (Mat a; CBS8340), CENPK-1 (Mat a, ura3), CENPK113ΔPDC1ΔPDC5ΔPDC6 (described above) and CENPK113ΔPDC2 (described above) yeast cells were grown in rich YPD complete medium (2% w/v yeast extract, 1% w/v peptone, 2% w/v glucose) until a concentration of $2 \times 10^7$ cells/ml, washed once in 0.1M lithium acetate, 1 mM EDTA, 10 mM Tris-HCl, pH 8, harvested, and resuspended in 0.1M lithium acetate, 1 mM EDTA, 10 mM Tris-HCl, pH 8, at a concentration of $2 \times 10^9$ cells/ml. 100 μl of the cellular suspension were incubated 5 minutes with 5–10 μg of vector (i.e, previously linearized in the auxotrophic marker in the case of pLC5, pLC7, pB1, pBST2, pBME2, pLC5-kanMX, pJEN1). After the addition of 280 μl of PEG 4000, the cells were incubated for at least 45' at 30°. 43 μl of DMSO were added and the suspension was incubated 5' at 42°. The cells were washed twice with water and plated onto selective medium. For the isolation of CENPK-1 strain (ura3), CENPK113 cells were grown in media containing 5-fluoorotic acid (see also above).

Single transformed clones were scored with 0.7% w/v Yeast Nitrogen Base, 2 w/v % glucose, 2 w/v % agar plus the appropriate supplements or G418 as indicated. For selection of G418$^R$ transformants, cells were also scored on 2 w/v % glucose, 2 w/v % Peptone, 1 w/v % Yeast extract, 2 w/v % agar, 200 μg/ml G418 (Gibco BRL, cat. 11811-031.

Transformed strain: supplements.
GRF18U[pLAT-ADH]: 200 mg/l uracile, 200 mg/l leucine, 200 mg/l histidine, 200 mg/l G418.
GRF18U[PB1]:200 mg/l leucine, 200 mg/l histidine.
GRF18U[pLC5]:200 mg/l leucine, 200 mg/l histidine.
GRF18U[pLC5][pLC7]:200 mg/l leucine.
GRF18U[pBM2]:200 mg/l leucine, 200 mg/l histidine.
GRF18U[pBST2]:200 mg/l leucine, 200 mg/l histidine.
GRF18U[pLC5][pJEN1]:200 mg/l leucine.
GRF18UΔPDC2[pLC5]:200 mg/l leucine, 200 mg/l histidine.
CENPK-1[PLC5]:no supplements
CENPK113[pLC5-KanMX]: 200 mg/l G418
CENPK113ΔPDC1ΔPDC5ΔPDC6[pLC5-KanMX]: 200 mg/l G418
CENPK113ΔPDC2[pLC5-KanMX]: 200 mg/l G418

List of the Expression Vectors Used:

| Name: | LDH source | promoter | Host, Selective marker |
|---|---|---|---|
| pEPL2 | Bovine | KLPDCA | K. Lactis, URA3. (FIG. 4) |
| pEPL4 | L. casei | KLPDCA | K. Lactis, URA3. |
| PLAZ10 | Bovine | KLPDCA | K. Lactis, APT1. |

-continued

| Name: | LDH source | promoter | Host, Selective marker |
|---|---|---|---|
| pLC5 | L. casei | SCTPI | S. cerevisiae, URA3. (FIG. 5) |
| pLC5-kanMx | L. casei | SCTPI | S. cerevisiae, APT1. |
| pBME2 | B. megaterium | SCTPI | S. cerevisiae, URA3. |
| pBST2 | B. Ste.- | SCTPI | S. cerevisiae, URA3. |
| pB1 | Bovine | SCTPI | S. cerevisiae, URA3. |
| pLC7 | L. casei | SCTPI | S. cerevisiae, HIS3. |
| pJEN1 | ////// | SCTPI | S. cerevisiae, HIS3. |
| pLAT-ADH | Bovine | SCADH1 | S. cerevisiae, APT1-URA3(FIG. 6) T. delbrueckii, APT1-URA3, Z. bailii, APT1-URA3. |

KL = K. lactis's promoter
SC = S. cerevisiae's promoter
B. Ste. = Bacillus stearothermophylus pJEN1 has been used for the overexpression of the JEN1 gene.

Batch Tests

Batch Analysis of *Kluyveromyces* PM6-7A[pEPL2], PMI/C1[pEPL2], PM6-7A[pEPL4] and PMI/C1[pEPL4] Transformed Cells.

Clones obtained by the transformation procedure above described were tested in batch culture during growth on minimum synthetic medium (1.3% w/v Yeast Nitrogen Base—aa (Difco, Detroit, Mich.), 200 mg/l adenine, 50 g/l glucose). The media used were both buffered or not with 200 mM phosphate buffer to a pH of 5.6.

Cells were preinoculated in the same test's medium. Exponentially growing cells were inoculated in flask (300 ml volume) containing 100 ml of fresh medium. The flasks were incubated at 30° C. in a shaking bath (Dubnoff, 150 rpm), and fermentation was monitored at regular time points. Cell number concentration was determined with an electronic Coulter counter (Coulter Counter ZBI Coulter Electronics Harpenden, GB, Porro et al., Res. Microbiol. (1991) 142, 535–539), after sonication of the samples to avoid cellular aggregates (Sonicator Fisher 300, medium point, Power 35%, 10 seconds)(FIGS. 7 and 8 and Tab.3)

Batch Analysis of *Kluyveromyces* BM3-12D[pLAZ10] Transformed Cells.

Clones obtained by the procedure above described were tested in batch culture during growth on minimum synthetic medium (1.3% w/v Yeast Nitrogen Base—aa (Difco, Detroit, Mich.), 50 g/l glucose, 20 gr/l ethanol, 200 mg/l G418). The media used were buffered with 200 mM phosphate buffer to a pH of 5.6.

Cells were preinoculated in the same test's medium. Exponentially growing cells were inoculated in flask (300 ml volume) containing 100 ml of fresh medium. The flasks were incubated at 30° C. in a shaking bath (Dubnoff, 150 rpm), and fermentation was monitored at regular intervals. Cell number concentration was determined with an electronic Coulter counter (Coulter Counter ZBI Coulter Electronics Harpenden, GB, Porro et al., Res. Microbiol. (1991) 142, 535–539), after sonication of the samples to avoid cellular aggregates (Sonicator Fisher 300, medium point, Power 35%, 10 seconds). At the beginning, cells used ethanol and then transformed glucose to lactic acid with very high yield (>0.75; g of lactic acid/g glucose consumed) (Tab.3).

Batch Analysis of *Torulaspora* CBS817[pLAT-ADH] Transformed Cells.

Clones obtained by the transformation procedure above described were tested in batch culture during growth on minimum synthetic medium (1.3% w/v Yeast Nitrogen Base—aa (Difco, Detroit, Mich.), 20 g/l glucose, 200 mg/l G418). The media used were not buffered.

Cells were preinoculated in the same test's medium. Exponentially growing cells were inoculated in flask (300 ml volume) containing 100 ml of fresh medium. The flasks were incubated at 30° C. in a shaking bath (Dubnoff, 150 rpm), and fermentation was monitored at regular intervals. Cell number concentration was determined with an electronic Coulter counter (Coulter Counter ZBI Coulter Electronics Harpenden, GB, Porro et al., Res. Microbiol. (1991) 142, 535–539), after sonication of the samples to avoid cellular aggregates (Sonicator Fisher 300, medium point, Power 35%, 10 seconds)(FIG. 10 and Tab.3)

Batch Analysis of *Zygosaccharomyces* ATCC36947 [pLAT-ADH] and ATCC60483[pLAT-ADH] Transformed Cells.

Clones obtained by the transformation procedure above described were tested in batch culture during growth on minimum synthetic medium (1.3% w/v Yeast Nitrogen Base—aa (Difco, Detroit, Mich.), 50 g/l glucose, 200 mg/l G418). The media used were not buffered.

Figure 11:
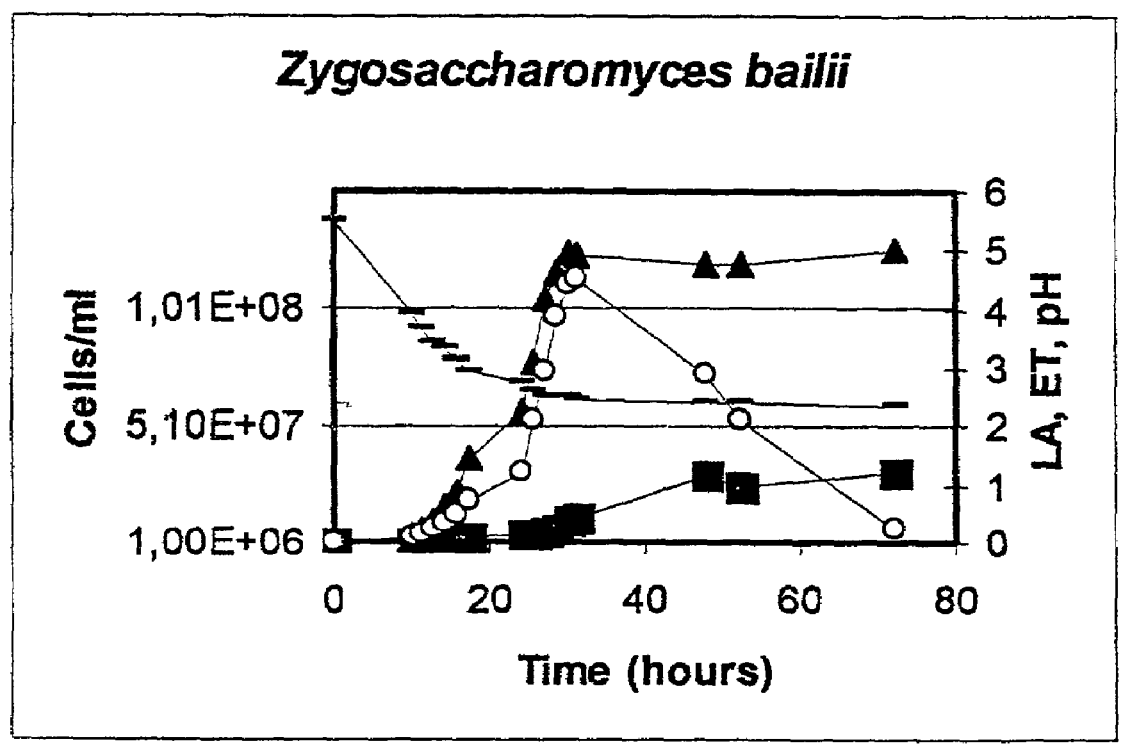

Cells were preinoculated in the same test's medium. Exponentially growing cells were inoculated in flask (300 ml volume) containing 100 ml of fresh medium. The flasks were incubated at 30° C. in a shaking bath (Dubnoff, 150 rpm), and fermentation was monitored at regular intervals. Cell number concentration was determined with an electronic Coulter counter (Coulter Counter ZBI Coulter Electronics Harpenden, GB, Porro et al., Res. Microbiol. (1991) 142, 535–539), after sonication of the samples to avoid cellular aggregates (Sonicator Fisher 300, medium point, Power 35%, 10 seconds)(FIG. 11 and Tab.3).

Batch Analysis of *Saccharomyces* GRF18Ur[pLAT-ADH], GRF18U[pB1], GRF18U[pLC5], GRF18U[pLC5] [pLC7], GRF18U[pBM2], GRF18U[pBST2], CENPK-1 [pLC5] Transformed Cells.

Clones obtained by the transformation procedure above described were tested in batch culture during growth on minimum synthetic medium (1.3% w/v Yeast Nitrogen Base—aa (Difco, Detroit, Mich.), 50 g/l glucose and appropriate supplements (see above). The media used were not buffered. Cells were preinoculated in the same test's medium. Exponentially growing cells were inoculated in flask (300 ml volume) containing 100 ml of fresh medium. The flasks were incubated at 30° C. in a shaking bath (Dubnoff, 150 rpm), and fermentation was monitored at regular intervals. Cell number concentration was determined with an electronic Coulter counter (Coulter Counter ZBI Coulter Electronics Harpenden, GB, Porro et al., Res. Microbiol. (1991) 142, 535–539), after sonication of the samples to avoid cellular aggregates (Sonicator Fisher 300, medium point, Power 35%, 10 seconds)(Tab.3).

Batch Analysis—Spinner Flask—of *Saccharomyces*, GRFL18UΔPDC2[pLC5], CENPK113[plC5-kanMX], CENPK113ΔPDC2[plC5-kanMXI] and CENPK113ΔPDC1ΔPDC5ΔPDC6[plC5-kanMX] Transformed Cells.

Clones obtained by the procedures above described were tested in batch culture during growth on rich medium (1.0% w/v Yeast Extract, 2% w/v Peptone, 100 gr/l glucose). The media were not buffered.

Cells were preinoculated on Yeast Extract-Peptone+ethanol (5 g/l) media. 100 ml were inoculated in spinner flasks (1.5 l working volume; initial pH=5.7). The spinner flasks were incubated at 30° C., agitation: 55 rmp. Fermentation was monitored at regular intervals (Tables A,B,C and Table 3).

The LDH specific activity from the different transformed strains, was higher than 5 U/mg of total cell proteins.

LDH Activity Dosage

Bovine LDH. About $10^8$ cells were harvested, washed in 50 mM phosphate buffer, pH 7.5, and resuspended in the same buffer. Cells were lysed with 5 cycles of vigorous vortexing in presence of glass microbeads (diameter 400 μm, SIGMA, G-8772) at 4° C. Cellular debris were removed by centrifugation (Eppendorf, Hamburg, D 5415 C, 13600 RCF, 10 min), and protein extracts'concentration was determined by Micro Assay, Biorad, Hercules, Calif. (cat. 500-0006).

About 0.2 mg of extract were tested for LDH activity using SIGMA (St. Louis, Mo.) kit DG1340-UV, according to manufacturer's instructions.

Bacterial LDHs. About $10^8$ cells were harvested, washed in 50 mM phosphate buffer, pH 7.5, and resuspended in the same buffer. Cells were lysed with 5 cycles of vigorous vortexing in presence of glass microbeads (diameter 400 μm, SIGMA, G-8772) at 4° C. Cellular debris were removed by centrifugation (Eppendorf, Hamburg, D 5415 C, 13600 RCF, 10 min), and protein extracts'concentration was determined by Micro Assay, Biorad, Hercules, Calif. (cat. 500-0006).

Cellular extract was tested for LDH activity using:

0,01 ml of 12.8 mM NADH 0,1 ml of 2 mM fructose1,6-diphosphate 0.74 ml of 50 mM acetate buffer (pH=5,6)

0,05 ml of properly diluted cell extract and 0,1 ml sodium pyruvate 100 mM.

LDH activity was assayed as micromoles of NADH oxidased per min, per mg of total cell extract at 340 nm, 25° C.

Metabolites dosage in the growth medium.

Samples from the growth medium, obtained after removing cells by centrifugation, were analysed for the presence of glucose, ethanol, L(+)- and D(−)-lactic acid using kits from Boehringer Mannheim, Mannheim Del., (#. 716251, 176290, and 1112821 respectively), according to manufacturer's instructions.

Experimental batch tests related to the *Kluyveromyces* PM6-7A[pEPL2] and PMI/C1[pEPL2] transformed yeasts are shown in FIGS. 7A, 7B and FIGS. 8A, 8B.

Experimental data related to the *Torulaspora* CBS817 [pLAT-ADH] transformed yeasts are shown in FIG. 10.

Experimental data related to the *Zyaosaccharomyces* ATCC60483 [pLAT-ADH] transformed yeasts are shown in FIG. 11.

Experimental data related to the *Saccharomyces* CENPK113[pLC5-KanMX] CENPK113ΔPDC2[pLC5-kanMX] and CENPK113ΔPDC1ΔPDC5ΔPDC6 [pLC5-kanMX] transformed yeasts growing in spinner-flask are shown in Tables A,B,C.

TABLE A

Overview of the cultivation with *S. cerevisae* (CENPK113[pLC5-KanMX])

| Time [h] | pH | OD$_{660}$ | glucose [g.l$^{-1}$] | ethanol [g.l$^{-1}$] | lactate [g.l$^{-1}$] |
|---|---|---|---|---|---|
| 0.0 | 5.76 | 0.31 | 88.4 ± 0.3 | 0.2 | 0 |
| 19.0 | 3.01 | 8.7 ± 0.2 | 6.5 ± 0.1 | 25 | 27.4 ± 0.2 |
| 25.0 | 3.05 | 10.41 ± 0.01 | 0.4 ± 0.2 | 27 | 30.1 ± 0.4 |
| 45.25 | 3.07 | 13.2 ± 0.2 | 0.06 ± 0.03 | 27 | 31.1 ± 0.2 |
| 70.75 | 3.08 | 10.6 ± 0.3 | 0 | 26 | 30.7 ± 0.1 |
| 92.0 | 3.08 | 12.2 ± 0.8 | 0 | 26 | 29.5 ± 0.1 |

TABLE B

Overview of the cultivation with *S. cerevisiae* (CEN.PK113 Δpdc2[pLC5-KanMX])

| Time [h] | pH | OD$_{660}$ | glucose [g.l$^{-1}$] | ethanol [g.l$^{-1}$] | lactate [g.l$^{-1}$] |
|---|---|---|---|---|---|
| 0.0 | 5.75 | 0.32 | 87 ± 0.4 | 0.2 | 0 |
| 19.0 | 3.20 | 2.2 ± 0.2 | 47.8 ± 0.1 | 8 | 17.3 ± 0.1 |
| 25.0 | 3.07 | 4.45 ± 0.1 | 36.3 ± 0.1 | 11 | 25.4 ± 0.1 |
| 45.25 | 2.96 | 5.31 ± 0.02 | 24.0 ± 0.1 | 15 | 38.0 ± 0.1 |
| 70.75 | 2.98 | 4.8 ± 0.1 | 12.9 ± 0.1 | 19 | 42.4 ± 0.4 |
| 92.0 | 2.95 | 5.3 ± 0.1 | 8.47 ± 0.01 | 24 | 43.1 ± 0.1 |

TABLE C

Overview of the cultivation with *S. cerevisiae* (CENPK113 Δpdc1 Δpdc5 Δpdc6 [pLC5-KanMX]

| Time [h] | pH | OD$_{660}$ | glucose [g.l$^{-1}$] | ethanol [g.l$^{-1}$] | lactate [g.l$^{-1}$] |
|---|---|---|---|---|---|
| 0.0 | 5.74 | 0.82 ± 0.01 | 92 ± 1 | | 0.171 ± 0.005 |
| 10.0 | 5.16 | 1.185 ± 0.02 | 93 ± 1 | | 0.715 ± 0.0 |
| 23.5 | 4.61 | 1.28 ± 0.03 | 94 ± 2 | | 1.76 ± 0.1 |
| 49.25 | 4.05 | 1.36 ± 0.03 | 92.8 ± 0.8 | | 3.614 ± 0.005 |
| 73.0 | 3.79 | 1.27 ± 0.03 | 89.0 ± 0.7 | | 5.17 ± 0.01 |
| 106.0 | 3.60 | 1.25 ± 0.02 | 80 ± 2 | | 6.84 ± 0.06 |
| 122.5 | 3.57 | 1.23 ± 0.05 | 81.24 ± 0.06 | 0 | 7.596 ± 0.006 |
| 167.0 | 3.43 | 1.17 ± 0.08 | 75 ± 1 | | 8.5 ± 0.2 |

All the results obtained from transformed *Kluyveromyces*, *Torulaspora*, *Zygosaccharomyces* and *Saccharomyces* yeasts are summarized and compared in Table 3. The yield is the amount of lactic acid produced (gr/l) divided by the amount of glucose consumed (gr/l). The percentage of free lactic acid is obtained from the Henderson-Hasselbalch equation: pH=pKa+log[(% Lactate)/(% Free Lactic Acid)], where the pK$_a$ for lactic acid is 3.86.

Comparison of the data reported in Table 3A Vs Table 3B clearly proves that in different yeasts genera, the production of lactic acid with higher yield on glucose can be obtained by changing the relative ratio—at cellular level—of the LDH and PDC activities. Such goal can be obtained following at least two different approaches:

(1) by reducing the PDC activity (compare data from transformed *K. lactis* hosts: PM6-7A Vs PMI/CI; compare data from transformed *S. cerevisiae* hosts GRF18U Vs GRF18ΔPDC2 and CENPK113 Vs CENPK113ΔPDC2 and CENPK113ΔPDC1ΔPDC5ΔPDC6)

(2) by increasing the LDH gene copy number and therefore the LDH activity (compare data from *S. cerevisiae* host: GRF18U[pLC5] Vs GRF18U[pLC5][pLC7]; the LDH heterolgous activity in the two strains is 5–6 and 7–8 U/mg of total cell proteins, respectively).

Further, higher yields can be obtained by manipulating the composition of the growth medium. Also in this case, a reduced ethanol production was observed (see also Table 4).

yeast. Res. in Microbiol., 142, 535–539, 1991). In the synthetic medium used, the source of Mg and Zn salts are $MgSO_4$ (5 mM) and $ZnSO_4 \times 7H_2O$ (0.02 mM), respectively.

TABLE 3A

BATCH TESTS. Lactic Acid Production from transformed Kluvveromyces lactis, Torulaspora delbrueckii, Zygosaccharomyces bailii and Saccharomyces cerevisiae yeasts bearing a heterologous LDH gene.

|  | Phosphate Buffer | Lactic Acid (g/L) | Yield (g/g) | Final pH | % Free Lactic Acid |
|---|---|---|---|---|---|
| | | Kluyveromyces yeasts | | | |
| PM6-7A (negative control) | − | 0.0 | 0.000 | 2.5 | 00 |
| PM6-7A[pEPL2] (FIG.7) | − | 1.2 | 0.024 | 2.0 | 99 |
| PM6-7A[pEPL2] (FIG.7) | + | 4.3 | 0.087 | 3.0 | 88 |
| PM6-7A[pEPL4] | − | 1.1 | 0.022 | 2.1 | 99 |
| PM6-7A[pEPL4] | + | 4.5 | 0.090 | 3.0 | 88 |
| | | Torulaspora yeasts | | | |
| CBS817(negative control) | − | 0.0 | 0.000 | 2.9 | 00 |
| CB5817[pLAT-ADH] (FIG.10) | − | 1.0 | 0.058 | 2.8 | 92 |
| | | Zygosaccharomyces yeasts | | | |
| ATCC60483(negative control) | − | 0.0 | 0.000 | 2.5 | 00 |
| ATCC60483[pLAT-ADH] (FIG. 11) | − | 1.2 | 0.029 | 2.4 | 96 |
| ATCC36947(negative control) | − | 0,0 | 0.000 | 2.5 | 00 |
| ATCC36947[pLAT-ADH] | − | 0,9 | 0.018 | 2.4 | 95 |
| | | Saccharomyces yeasts | | | |
| GRF18U(negative control) | − | 0.0 | 0.000 | 3.1 | 00 |
| GRF18U[pLAT-ADH] | − | 2.1 | 0.040 | 3.0 | 88 |
| GRF18U[pLC5] | − | 8.297 | 0.165 | 3.0 | 88 |
| GRF18U[pBME2] | − | 5.927 | 0.118 | 3.0 | 88 |
| GRF18U[pBST2] | − | 0.320 | 0.06 | 3.1 | 87 |
| GRF18U[pB1] | − | 1.5 | 0.020 | 3.0 | 88 |
| CENPK-1[pLC5] | − | 1.8 | 0.030 | 3.0 | 88 |
| **CENPK113[pLC5-KanMX] | − | 29.5 | 0.338 | 3.0 | 88 |

TABLE 3B

BATCH TESTS. Lactic acid yield can be improved by both genetic and physiological approaches (compare with table 3A).

|  | Phosphate Buffer | Lactic Acid (g/L) | Yield (g/g) | Final pH | % Free Lactic Acid |
|---|---|---|---|---|---|
| | | Kluyveromyces yeasts: | | | |
| PMI/C1ΔPDCA[pEPL2] (FIG.8) | − | 2.0 | 0.052 | 2.3 | 97 |
| PMI/C1ΔPDCA[pEPL2] (FIG.8) | + | 11.4 | 0.233 | 2.9 | 90 |
| PMI/C1ΔPDCA[pEPL4] | − | 2.1 | 0.053 | 2.3 | 97 |
| PMI/C1ΔPDCA[pEPL4] | + | 11.0 | 0.231 | 2.9 | 90 |
| BM3-12D[pLAZ10] | + | 20.5 | 0.757 | 3.5 | 70 |
| | | Saccharomyces yeasts | | | |
| GRF18U[pLC5][pLC7] | − | 9.867 | 0.197 | 3.0 | 88 |
| **GRF18UΔPDC2[pLC5] | − | 30.2 | 0.347 | 3,0 | 88 |
| **CENPK113 ΔPDC2[pLC5-KanMX] | − | 43.1 | 0.549 | 2.9 | 88 |
| **CENPK113 ΔPDC1,Δ5,Δ6[pLC5-KanMX] | − | 8.5 | 0.500 | 3.4 | 73 |
| §GRF18U[pLC5][pLC7] | − | 13.74 | 0.29 | 3.0 | 88 |

(§: see also Table 4 for more details about this last data)
**data obtained in spinner flask, under partial anaerobic conditions (see also Tables A, B, C)

Experimental Data Related to the Saccharomyces GRF18 [pLC5][pLC7] Growing in a Manipulated Mineral Medium (Table 4).

Lactic acid production by Saccharomyces GRF18U [pLC5][pLC7] transformed cells was also carried out growing the cells in a synthetic medium (D. Porro et al., Development of a pH controlled fed-batch system for budding Production was tested in aerobic batch culture (glucose concentration 50 gr/l) as above described for the other transformed Saccharomyces cells. It has been found that depletion of both $MgSO_4$ and $ZnSO_4 \times 7H_2O$ yielded higher yield and higher lactic acid productivities. In fact, these minerals could be required as cofactor for the enzymatic activities leading to ethanol production. Data are shown in Table 4.

TABLE 4

L(+) L-lactic acid production by Saccharomyces
GRF18[pLC5][pLC7] transformed cells during batch growth
in manipulated mineral media.

|  | Control | -Mg | -Zn |
|---|---|---|---|
| Lactic acid production, g/l | 9.23 | 13.74 | 13.74 |
| Yield, g/g | 0.20 | 0.29 | 0.29 |
| Productivity, g/l, hr | 0.38 | 0.42 | 0.61 |
| Ratio ethanol/lactic acid, mM/mM | 2.78 | 2.11 | 1.99 |

Legend:

Control: complete synthetic medium (Res. in Microbiol., 142, 535–539, 1991; enclosed)

-Mg: identical to the control but with out $MgSO_4$

-Zn: identical to the control but with out $ZnSO_4 \times 7H_2O$

For all the tests, the final pH value was lower than 3.0 and therefore the % of free lactic acid was higher than 88%.

Lactic Acid Production by Yeast Cells Overexpressing the JEN1 Gene.

Better lactic acid productions and lower ethanol productions have been obtained by overexpression of the JEN1 gene, encoding for the lactate transporter.

GRF18U[pLC5] (i.e, negative control) and GRF18U [pLC5][pJEN1] have been grown in media containing 2% glucose, 0.67% YNB and supplements (i.e., 100 mg/l leucine-histidine, and 100 mg/l leucine, respectively).

Cells were preinoculated in the same test's medium. Exponentially growing cells were inoculated in flask (300 ml volume) containing 100 ml of fresh medium. The flasks were incubated at 30° C. in a shaking bath (Dubnoff, 150 rpm), and fermentation was monitored at regular intervals. Cell number concentration was determined with an electronic Coulter counter (Coulter Counter ZBI Coulter Electronics Harpenden, GB, Porro et al., Res. Microbiol. (1991) 142, 535–539), after sonication of the samples to avoid cellular aggregates (Sonicator Fisher 300, medium point, Power 35%, 10 seconds).

TABLE 5

Comparison of lactate and ethanol
productions during batch cultures

| Strain | Lactate g/l | Ethanol g/l |
|---|---|---|
| GRF18U[pLC5] | 3,33 | 4,39 |
| GRF18U[pLC5][pJEN1] | 6,06 | 4,23 |

Continuous Lactic Acid Production.

Continuous and stable productions of lactic acid have been obtained for more than 2 weeks by means of classical chemostat cultures (the continuous flow of fresh medium to the bioreactor supported specific growth rate ranging between 0,01 and 0,3 $hr^{-1}$) using both the transformed *K. lactis* PM6-7A[pEPL2], PMI/CI[pEPL2] and the transformed *S. cerevisiae* GRF18U[pLC5][pLC7] strains.

Fed-Batch Tests

Lactic Acid Production by PMI/C1[pEPL2] in a Stirred-tank Fermentor

Lactic acid production by PMI/C1[pEPL2] was further tested by cultivation in a 14-liter stirred-tank farmentor containing 8 liters of nutrient medium (30 g dry solids/L light corn steep water, A. E. Staley Manufacturing Co., Decatur, Ill.; 10 g/L Difco yeast extract, Difco, Detroit, Mich.; 200 mg/L adenine, 50 g/L glucose). The fermentor was kept at 300° C., agitated at 400 rpm, and aerated at 2 liters/min throughout. Antifoam (Antifoam 1520, Dow Corning Corp., Midland, Mich.) was added as needed to control foaming. Glucose was fed as needed to maintain a residual concentration in the fermentation medium of about 25–50 g/L. When controlled, the pH was maintained by automatic addition of 14.8 M ammonium hydroxide in water. Lactic acid production at acidic pH was tested as follows: (1) The fermentation pH was controlled at 4.5 throughout the fermentation. (2) The initial fermentation pH was controlled at 4.0 until 80 mL of 14.8 M ammonium hydroxide were added. Then pH control was discontinued. (3) The initial fermentation pH was 5.0 and no neutralizing agent was added during the fermentation. The results are shown in Table 6. The elapsed time was measured from the time of inoculation. Samples from the fermentation, obtained after removing cells by filtration, were analyzed for the presence of glucose and L(+)-lactic acid using a YSI Model 2700 Select Biochemistry Analyzer (Yellow Springs Instrument Co., Inc., Yellow Springs, Ohio). Ethanol, measured by gas chromatography, was not detected in any of the fermentations. Yield and % free lactic acid were calculated as previously described. Inocula for the fermentations were prepared by pre-culturing PMI/C1[pEPL2] in 50 mL of minimum synthetic medium (1.3% w/v Yeast Nitrogen Base -aa (Difco, Detroit, Mich.), 200 mg/L adenine, 5 g/L ammonium sulfate, 50 g/L glucose) in a 250 mL baffled Erlenmeyer flasks for 30 hr at 30° C. and 300 rpm in an incubator shaker (Model G-24, New Brunswick Scientific Co., Inc., Edison, N.J.).

Similar results were obtained using the bacterial LDH gene (plasmid pEPL4; data not shown).

TABLE 6

Lactic Acid Production by Kluyveromyces PMI/C1[pEPL2] cells
in a Fermentor.

| | | | Lactic | | | |
|---|---|---|---|---|---|---|
| | Elapsed Time (hr) | NH₄OH Added (M) | Acid (g/L) | Yield (g/g) | Final pH | % Free Lactic Acid |
| Case 1 | 137 | 1.31 | 109 | 0.59 | 4.5 | 19 |
| Case 2 | 97 | 0.14 | 35 | 0.44 | 3.0 | 88 |
| Case 3 | 72 | 0 | 29 | 0.35 | 2.8 | 92 |

Lactic Acid Production by BM3-12D[pLAZ10] in a Stirred-tank Fermentor.

Lactic acid production by EM3-12D[pLAZ10] was further tested by cultivation in a 1 liter stirred-tank fermentor containing 0.8 liters of nutrient medium (6,7 gr/YNB/Yeast Nitrogen Base—Difco, Detroit, Mich., 45 g/L glucose, 2% v/v ethanol, G418 200 mg/l). The fermentor was kept at 30° C., agitated at 400 rpm, and aerated at 0.8 liters/min throughout. Antifoam (Antifoam 1520, Dow Corning Corp., Midland, Mich.) was added as needed to control foaming. Transformed cells first used ethanol for the production of biomass (first 50 hrs of growth) and then transformed glucose to L(+) Lactic acid. The pH was maintained at 4.5 by automatic addition of 2 M KOH. Glucose was fed as needed to maintain a residual concentration in the fermentation medium of about 35–45 g/L The results are shown in FIG. 9 and Table 7 (Case 1). The elapsed time was measured from the time of inoculation. Samples from the fermentation, obtained after removing cells by filtration, were analyzed for the presence of glucose, ethanol and L(+)-lactic acid using a standard enzymatic analysis as described in Porro et al. 1995 (supra). After T=50 hr, ethanol was not detected in any of sample-test. Yield and % free lactic acid were calculated as previously described.

Inocula for the fermentations were prepared by pre-culturing BM3-12D[pLAZ10] in 50 mL of minimum synthetic medium (1.3% w/v Yeast Nitrogen Base-aa (Difco, Detroit, Mich.), 2% v/v ethanol, G418 200 mg/l) in a 250 mL baffled Erlenmeyer flasks for 40 hr at 30° C and 300 rpm in an incubator shaker (Model G-24, New Brunswick Scientific Co., Inc., Edison, N.J.).

In a different experiment (Table 7, Case 2), the initial fermentation pH was 5.4 and no neutralizing agent was added during the fermentation.

TABLE 7

Lactic Acid Production by Kluyveromyces BM3-12D[pLAZ10] cells in Fermentor.

| | Elapsed Time (hr) | Lactic Acid (g/L) | Yield (g/g) | Final pH | % Free Lactic Acid |
|---|---|---|---|---|---|
| Case 1 | 474 | 60.3 | 0.854 | 4.5 | 19 |
| Case 2 | 498 | 32.3 | 0.881 | 3.6 | 65 |

The invention claimed is:

1. A process for the preparation of lactic acid, comprising:
growing, in a fermentation medium containing a carbon source, a yeast strain transformed with at least one copy of a gene coding for lactate dehydrogenase functionally linked to a promoter sequence allowing the expression of the gene in the yeast stain, wherein the yeast strain produces lactic acid at a yield from 0.5 gram lactic acid per gram glucose to 0.881 gram lactic acid per gram glucose, and wherein the transformed yeast strain has undergone deletion of one or more pyruvate decarboxylase genes or pyruvate dehydrogenase genes, to produce lactic acid, wherein the yeast strain can grow or maintain its population at the pH of the fermentation medium, wherein the initial pH of the fermentation medium is higher than 4.5; and,
recovering the lactic acid from the fermentation medium.

2. The process of claim 1, wherein the carbon source is selected from glucose, fructose, galactose, lactose, sucrose, raffinose, maltose, cellobiose, arabinose, or xylose.

3. The process of claim 1, wherein the fermentation medium contains less than 5 mM of $Mg^{++}$, less than 0.02 mM of $Zn^{++}$, or both.

4. The process of claim 1, wherein at the time recovering is performed the fermentation medium has a pH of 7 or less.

5. The process of claim 4, wherein at the time recovering is performed the fermentation medium has a pH of 4.5 or less.

6. The process of claim 5, wherein at the time recovering is performed the fermentation medium has a pH of 3 or less.

7. The process of claim 1, wherein the lactic acid is D-lactic acid or L-lactic acid.

8. The process of claim 1, wherein recovering comprises extracting lactic acid into an immiscible solvent phase.

9. The process of claim 1, wherein recovering comprises distillation of lactic acid or an ester thereof.

* * * * *

UNITED STATES PATENT AND TRADEMARK OFFICE
CERTIFICATE OF CORRECTION

PATENT NO. : 7,049,108 B2
APPLICATION NO. : 10/068137
DATED : May 23, 2006
INVENTOR(S) : Danilo Porro et al.

It is certified that error appears in the above-identified patent and that said Letters Patent is hereby corrected as shown below:

Column 33, line 61, delete "stain" and insert -- strain --.

Signed and Sealed this

Eleventh Day of July, 2006

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligomer anneals to inactivated ampicillin
      resistance gene of plas

<400> SEQUENCE: 1
gttgccattg ctgcaggcat cgtggtg                                        27

<210> SEQ ID NO 2
<211> LENGTH: 29
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligomer anneals upstream of Bos taurus LDH
      gene in 5'UTR and crea

<400> SEQUENCE: 2
cctttagggt ctagatccaa gatggcaac                                      29

<210> SEQ ID NO 3
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligomer anneals to 5' end of L. casei LDH gene
      and introduces a N

<400> SEQUENCE: 3
ccatggcaag tattacggat aaggatc                                        27

<210> SEQ ID NO 4
```

-continued

```
<211> LENGTH: 24
<212> TYPE: DNA
<213> ORGANISM: Lactobacillus casei
<220> FEATURE:
<221> NAME/KEY: misc_feature
<222> LOCATION: ()..()
<223> OTHER INFORMATION: Antisense oligomer anneals 8 bp upstream of  3'
      end of L. casei LD

<400> SEQUENCE: 4
ctatcactgc agggtttcga tgtc                                             24

<210> SEQ ID NO 5
<211> LENGTH: 59
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligomer  complementary to S. cerevisiae PDC1
      and anneals to loxP -

<400> SEQUENCE: 5
ttctactcat aacctcacgc aaaataacac agtcaaatca cagctgaagc ttcgtacgc       59

<210> SEQ ID NO 6
<211> LENGTH: 62
<212> TYPE: DNA
<213> ORGANISM: Artificial Sequence
<220> FEATURE:
<221> NAME/KEY: misc_feature
<222> LOCATION: ()..()
<223> OTHER INFORMATION: Antisense oligomer  complementary to S.
      cerevisiae PDC1 and annea l

<400> SEQUENCE: 6
aatgcttata aaactttaac taataattag agattaaatc gcataggcca ctagtggatc      60
tg                                                                    62

<210> SEQ ID NO 7
<211> LENGTH: 59
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligomer  complementary to S. cerevisiae PDC5
      and anneals to loxP-

<400> SEQUENCE: 7
atcaatctca aagagaacaa cacaatacaa taacaagaag cagctgaagc ttcgtacgc       59

<210> SEQ ID NO 8
<211> LENGTH: 62
<212> TYPE: DNA
<213> ORGANISM: Artificial Sequence
<220> FEATURE:
<221> NAME/KEY: misc_feature
<222> LOCATION: ()..()
<223> OTHER INFORMATION: Antisense oligomer  complementary to S.
      cerevisiae  PDC5 and annea

<400> SEQUENCE: 8
aaaatacaca aacgttgaat catgagtttt atgttaatta gcataggcca ctagtggatc      60
tg                                                                    62

<210> SEQ ID NO 9
```

-continued

```
<211> LENGTH: 59
<212> TYPE: DNA
<213> ORGANISM: Artificial Sequence
<220> FEATURE:
<221> NAME/KEY: misc_feature
<222> LOCATION: ()..()
<223> OTHER INFORMATION: Oligomer  complementary to S. cerevisiae PDC6
      and anneals to loxP-

<400> SEQUENCE: 9
taaataaaaa acccacgtaa tatagcaaaa acatattgcc cagctgaagc ttcgtacgc      59

<210> SEQ ID NO 10
<211> LENGTH: 62
<212> TYPE: DNA
<213> ORGANISM: Artificial Sequence
<220> FEATURE:
<221> NAME/KEY: misc_feature
<222> LOCATION: ()..()
<223> OTHER INFORMATION: Antisense oligomer  complementary to S.
      cerevisiae PDC6 and annea l

<400> SEQUENCE: 10
tttatttgca acaataattc gtttgagtac actactaatg gcataggcca ctagtggatc     60
tg                                                                    62

<210> SEQ ID NO 11
<211> LENGTH: 59
<212> TYPE: DNA
<213> ORGANISM: Artificial Sequence
<220> FEATURE:
<221> NAME/KEY: misc_feature
<222> LOCATION: (1)..(2)
<223> OTHER INFORMATION: to be provided

<400> SEQUENCE: 11
acgcaacttg aattggcaaa atgggcttat gagacgttcc cagctgaagc ttcgtacgc      59

<210> SEQ ID NO 12
<211> LENGTH: 62
<212> TYPE: DNA
<213> ORGANISM: Artificial Sequence
<220> FEATURE:
<221> NAME/KEY: misc_feature
<222> LOCATION: ()..()
<223> OTHER INFORMATION: Antisense oligomer  complementary to S.
      cerevisiae PDC2 and annea l

<400> SEQUENCE: 12
agcctgtgtt accaggtaag tgtaagttat tagagtctgg gcataggcca ctagtggatc     60
tg                                                                    62
```